(12) United States Patent
Sung et al.

(10) Patent No.: US 7,871,816 B2
(45) Date of Patent: Jan. 18, 2011

(54) VECTOR FOR ANTI-HPV VACCINE AND TRANSFORMED MICROORGANISM BY THE VECTOR

(75) Inventors: Moon-Hee Sung, Yuseong-gu (KR); Ha Ryoung Poo, Daejeon (KR); Jong Soo Lee, Anseong-si (KR); Chang Min Jung, Gangnam-gu (KR); Seung Pyo Hong, Yuseong-gu (KR); Chul-Joong Kim, Yuseong-gu (KR); Sue-nie Park, Seodaemoon-gu (KR); Hyun-mi Pyo, Seo-gu (KR)

(73) Assignees: Bioleaders Corporation (KR); Korea Research Institute of Bioscience and Biotechnology (KR)

( * ) Notice: Subject to any disclaimer, the term of this patent is extended or adjusted under 35 U.S.C. 154(b) by 238 days.

(21) Appl. No.: 11/939,546

(22) Filed: Nov. 13, 2007

(65) Prior Publication Data

US 2009/0117151 A1 May 7, 2009

Related U.S. Application Data

(62) Division of application No. 10/530,083, filed on Jun. 3, 2005, now Pat. No. 7,425,438.

(51) Int. Cl.
*C12N 1/20* (2006.01)
*C12N 15/00* (2006.01)
(52) U.S. Cl. .................................. 435/320.1; 435/252.3
(58) Field of Classification Search ........................ None
See application file for complete search history.

(56) References Cited

U.S. PATENT DOCUMENTS

2005/0249752 A1  11/2005  Sung et al.

FOREIGN PATENT DOCUMENTS

| JP | 2001-017182 A | 1/2001 |
|---|---|---|
| KR | 10-2001-0044019 A | 6/2001 |
| KR | 10-2004-0032824 A | 4/2004 |
| WO | 9901557 A1 | 1/1999 |
| WO | 0075336 A2 | 12/2000 |

OTHER PUBLICATIONS

Agterberg, Marja, et al., "Outer membrane PhoE protein of *Escherichia coli* as a carrier for foreign antigenic determinants: immunology of epitop . . . ", "Vaccine", Feb. 1990, pp. 85-91, vol. 8, No. 1.
Ashiuchi, Makoto, et al., "A Poly-gamma-glutamate Synthetic System of *Bacillus subtilis* IFO 3336: Gene Cloning and Biochemical Analysis of . . . ", "Biochem. Biophy. Res. Comm.", Sep. 16, 1999, pp. 6-12, vol. 263, No. 1.
Bubenik, J., et al., "Therapeutic vaccines against HPV16-associated tumors", "Neoplasma", 2002, pp. 285-289, vol. 49, No. 5.
Charbit, A., et al., "Presentation of two epitopes of the preS2 region of hepatitis B virus on live recombinant bacteria", "J. Immunol.", Sep. 1, 1987, pp. 1658-1664, vol. 139, No. 5.
Felici, Franco, et al., "Selection of antibody ligands from a large library of oligopeptides expressed on a multivalent exposition vector", "J. Mol. Biol.", Nov. 20, 1991, pp. 301-310, vol. 222, No. 2.
Fuchs, P., et al., "Targeting recombinant antibodies to the surface of *Excherichia coli*: fusion to a peptidoglycan associated lipoprotein", "Bio/Technology", Dec. 1991, pp. 1369-1372, vol. 9, No. 12.
Gao, L., et al., "Immune response to human papillomavirus type 16 E6 gene in a live vaccinia vector", "J. Gen. Virol.", Jan. 1994, pp. 157-164, vol. 75.
Hagensee, Michael E., et al., "Self-assembly of human papillomavirus type 1 capsids by expression of the L1 protein alone or by coexpression of the . . . ", "J. Virol.", Jan. 1993, pp. 315-322, vol. 67.
Hedegaard, Lisbeth, et al., "Type 1 fimbriae of *Escherichia coli* as carriers of heterologous antigenic sequences", "Gene", Dec. 21, 1989, pp. 115-124, vol. 85, No. 1.
Jung, Heung-Chae, et al., "Surface display of *Zymomonas mobilis* levansucrase by using the ice-nucleation protein of *Pseudomonas syringae*", "Nat. Biotech.", Jun. 1998, pp. 576-580, vol. 16, No. 6.
Jung, H.C., et al., "Expression of carboxymethylcellulase on the surface of *Escherichia coli* using *Pseudomonas syringae* ice nucleation . . . ", "Enzyme Microb. Technol.", Apr. 1998, pp. 348-354, vol. 22, No. 5.
Kornacker, M.G., et al., "The normally periplasmic enzyme beta-lactamase is specifically and efficiently translocated through the *Escherchia* . . . ", "Mol. Microbiol.", Jul. 1990, pp. 1101-1109, vol. 4, No. 7.
Koutsky, Laura A. et al., "A controlled trial of a human papillomavirus type 16 vaccine", "New England Journal of Medicine", 2002, pp. 1645-1651, vol. 347, No. 21.
Lee, Jong-Soo, et al., "Surface-displayed viral antigens on *Salmonella* carrier vaccine", "Nat. Biotech.", Jun. 2000, pp. 645-648, vol. 18, No. 6.
Lehtinen, M., et al., "Efficacy of preventive human papillomavirus vaccination", "Int. J. STD. AIDS", Dec. 2001, pp. 771-776, vol. 12, No. 12.
Meneguzzi, et al., "Immunization against human papillomavirus type 16 tumor cells with recombinant vaccinia viruses expressing E6 and E7", "Virology", 1991, pp. 62-69, vol. 181, No. 1.
Moss, Bernard, "Genetically engineered poxviruses for recombinant gene expression, vaccination, and safety", "Proc. Natl. Acad. Sci. USA", Oct. 1996, pp. 11341-11348, vol. 93.
Pfister, H., et al., "Human papillomaviruses and genital cancer", "Advanced Cancer Research", 1987, pp. 113-147, vol. 48.

(Continued)

*Primary Examiner*—Mark Navarro
(74) *Attorney, Agent, or Firm*—Kelly K. Reynolds; Steven J. Hultquist; Intellectual Property/Technology Law

(57) ABSTRACT

Expression vectors that can efficiently produce virion capsid protein, tumor-associated protein of human papillomavirus on a microbial surface. Bacterial strains harboring such surface display vectors, and the use of the bacterial strains or their extracts or purified products as complex vaccines, are also described. The surface display vectors contain one or more than two genes selected from among pgsB, pgsC and pgsA, encoding a poly-χ-glutamic acid synthetase complex (pgsBCA) of a *Bacillus* sp. strain, and genes that encode virion capsid proteins, tumor-associated proteins of human papillomavirus. Methods for preparing the foregoing vectors, vaccines and transformed microorganisms are also described.

17 Claims, 14 Drawing Sheets

OTHER PUBLICATIONS

Pisani, P., et al., "Estimates of the worldwide mortality from eighteen major cancers in 1985. Implications for prevention and projections . . . ", "Int. J. Cancer", 1993, pp. 891-903, vol. 55, No. 6.

Plotkin, Stanley A., M.D., et al., "Vaccines", "Vaccines", 1988, p. 571, Publisher: W. B. Saunders Co.

Ressing, et al., "Human CTL epitopes encoded by human papillomavirus type 16 E6 and E7 identified through in vivo and in vitro . . . ", "J. Immunol.", Jun. 1995, pp. 5934-5943, vol. 154, No. 11.

Schiller, John., et al., "Papillomavirus-like particles and HPV vaccine development", "Seminars in Cancer Biol.", Dec. 1996, pp. 373-382, vol. 7, No. 6.

Thanavala, Y., et al., "Immunogenicity of transgenic plant-derived hepatitis B surface antigen", "Proc. Natl. Acad. Sci. USA", Apr. 1995, pp. 3358-3361, vol. 92.

Francisco, Joseph A., et al., "Transport and anchoring of beta-lactamase to the external surface of *Escherichia coli*", "Proc. Natl. Acad. Sci. USA", Apr. 1, 1992, pp. 2713-2717, vol. 89, No. 7.

Lowy, Douglas R., et al., "Genital human papillomavirus infection", "Proc. Natl. Acad. Sci. USA", Mar. 1994, pp. 2436-2440, vol. 91.

Meneguzzi, et al., "Immunization against human papillomavirus type 16 tumor cells with recombinant vaccinia viruses expressing E6 and E7", "Virology", 1991, pp. 62-69, vol. 181, No. 1.

SEQUENCE LISTING

```
<160> NUMBER OF SEQ ID NOS: 11

<210> SEQ ID NO 1
<211> LENGTH: 1182
<212> TYPE: DNA
<213> ORGANISM: Bacillus subtilis

<400> SEQUENCE: 1
atgggctggt tactcattat agcctgtgct gtcatactgg tcatcggaat attagaaaaa    60
cgacgacatc agaaaaacat tgatgccctc cctgttcggg tgaatattaa cggcatccgc   120
ggaaaatcga ctgtgacaag gctgacaacc ggaatattaa tagaagccgg ttacaagact   180
gttggaaaaa caacaggaac agatgcaaga atgatttact gggacacacc ggaggaaaag   240
ccgattaaac ggaaacctca ggggccgaat atcggagagc aaaaagaagt catgagagaa   300
acagtagaaa gaggggctaa cgcgattgtc agtgaatgca tggctgttaa cccagattat   360
caaatcatct ttcaggaaga acttctgcag gccaatatcg gcgtcattgt gaatgtttta   420
gaagaccata tggatgtcat ggggccgacg cttgatgaaa ttgcagaagc gtttaccgct   480
acaattcctt ataatggcca tcttgtcatt acagatagta aatataccga gttctttaaa   540
caaaaagcaa agaacgaaa cacaaaagtc atcattgctg ataactcaaa aattacagat   600
gagtatttac gtaattttga atacatggta ttccctgata acgcttctct ggcgctgggt   660
gtggctcaag cactcggcat tgacgaagaa acagcattta agggaatgct gaatgcgccg   720
ccagatccgg gagcaatgag aattcttccg ctgatcagtc cgagcgagcc tgggcacttt   780
gttaatgggt ttgccgcaaa cgacgcttct tctactttga atatatggaa acgtgtaaaa   840
gaaatcggtt acccgaccga tgatccgatc atcatcatga actgccgcgc agaccgtgtc   900
gatcggacac agcaattcgc aaatgacgta ttgccttata ttgaagcaag tgaactgatc   960
ttaatcggtg aaacaacaga accgatcgta aaagcctatg aagaaggcaa aattcctgca  1020
gacaaactgc atgacctaga gtataagtca acagatgaaa ttatggaatt gttaaagaaa  1080
agaatgcaca accgtgtcat atatggcgtc ggcaatattc atggtgccgc agagccttta  1140
attgaaaaaa tccacgaata caaggtaaag cagctcgtaa gc                     1182

<210> SEQ ID NO 2
<211> LENGTH: 447
<212> TYPE: DNA
<213> ORGANISM: Bacillus subtilis

<400> SEQUENCE: 2
atgttcggat cagatttata catcgcacta attttaggtg tactactcag tttaattttt    60
gcggaaaaaa cagggatcgt gccggcagga cttgttgtac cggatatttt aggacttgtg   120
tttaatcagc cggtctttat tttacttgtt ttgctagtga gcttgctcac ttatgttatc   180
gtgaaatacg gtttatccaa attttatgatt ttgtacggac gcagaaaatt cgctgccatg   240
ctgataacag ggatcgtcct aaaaatcgcg tttgattttc tatacccgat tgtaccatttt   300 gaaatcgcag aatttcgagg aatcggcatc atcgtgccag gtttaattgc caataccatt   360
```

```
cagaaacaag gtttaaccat tacgttcgga agcacgctgc tattgagcgg agcgaccttt      420
gctatcatgt ttgtttacta cttaatt                                         447

<210> SEQ ID NO 3
<211> LENGTH: 1140
<212> TYPE: DNA
<213> ORGANISM: Bacillus subtilis

<400> SEQUENCE: 3
atgaaaaaag aactgagctt tcatgaaaag ctgctaaagc tgacaaaaaa gcaaaaaaag       60
aaaaccaata agcacgtatt tattgccatt ccgatcgttt ttgtccttat gttcgctttc      120
atgtgggcgg aaaagcgga aacgccgaag gtcaaaacgt attctgacga cgtactctca      180
gcctcatttg taggcgatat tatgatggga cgctatgttg aaaaagtaac ggagcaaaaa      240
ggggcagaca gtatttttca atatgttgaa ccgatcttta gagcctcgga ttatgtagca      300
ggaaactttg aaaacccggt aacctatcaa aagaattata acaagcaga taaagagatt       360 catctgcaga cgaataagga atcagtgaaa gtcttgaagg atatgaattt cacggttctc      420
aacagcgcca acaaccacgc aatggattac ggcgttcagg gcatgaaaga tacgcttgga      480
gaatttgcga agcaaaacct tgatatcgtt ggagcgggat acagcttaag tgatgcgaaa      540
aagaaaattt cgtaccagaa agtcaacggg gtaacgattg caacgcttgg ctttaccgat      600
gtgtccggga aggtttcgc ggctaaaaag aatacgccgg gcgtgctgcc cgcagatcct       660
gaaatcttca tccctatgat ttcagaagcg aaaaaacatg ctgacattgt tgttgtgcag      720
tcacactggg gccaagagta tgacaatgat ccaaacgacc gccagcgcca gcttgcaaga      780
gccatgtctg atgcgggagc tgacatcatc gtcggccatc atccgcacgt cttagaaccg      840
attgaagtat ataacggaac cgtcattttc tacagcctcg gcaactttgt ctttgaccaa      900
ggctggacga gaacaagaga cagtgcactg gttcagtatc acctgaagaa aaatggaaca      960
ggccgctttg aagtgacacc gatcgatatc catgaagcga cacctgcacc tgtgaaaaaa     1020
gacagcctta acagaaaac cattattcgc gaactgacga aagactctaa tttcgcttgg      1080
aaagtagaag acggaaaact gacgtttgat attgatcata gtgacaaact aaaatctaaa     1140

<210> SEQ ID NO 4
<211> LENGTH: 26
<212> TYPE: DNA
<213> ORGANISM: Artificial Sequence
<220> FEATURE:
<223> OTHER INFORMATION: Synthetic Construct

<400> SEQUENCE: 4
cgcggatcct ctctttggct gcctag                                           26

<210> SEQ ID NO 5
<211> LENGTH: 31
<212> TYPE: DNA
<213> ORGANISM: Artificial Sequence
<220> FEATURE:
<223> OTHER INFORMATION: Synthetic Construct

<400> SEQUENCE: 5
ggaaagcttt tattacagct tacgtttttt g                                     31

<210> SEQ ID NO 6
<211> LENGTH: 24
<212> TYPE: DNA
```

-continued

<213> ORGANISM: Artificial Sequence
<220> FEATURE:
<223> OTHER INFORMATION: Synthetic Construct

<400> SEQUENCE: 6
cgcggatccc caggaggtat gcat                                              24

<210> SEQ ID NO 7
<211> LENGTH: 29
<212> TYPE: DNA
<213> ORGANISM: Artificial Sequence
<220> FEATURE:
<223> OTHER INFORMATION: Synthetic Construct

<400> SEQUENCE: 7
ggaaagcttt tatggtttct gagaacaga                                         29

<210> SEQ ID NO 8
<211> LENGTH: 29
<212> TYPE: DNA
<213> ORGANISM: Artificial Sequence
<220> FEATURE:
<223> OTHER INFORMATION: Synthetic Construct

<400> SEQUENCE: 8
ctgggatccc aagtatgtt gcccgtttg                                          29

<210> SEQ ID NO 9
<211> LENGTH: 30
<212> TYPE: DNA
<213> ORGANISM: Artificial Sequence
<220> FEATURE:
<223> OTHER INFORMATION: Synthetic Construct

<400> SEQUENCE: 9
tgaagcttat taggacgatg ggatgggaat                                        30

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10
gcacatatgt tcggatcaga tttatacatc                                        30

<210> SEQ ID NO 11
<211> LENGTH: 30
<212> TYPE: DNA
<213> ORGANISM: Artificial Sequence
<220> FEATURE:
<223> OTHER INFORMATION: Synthetic Construct

<400> SEQUENCE: 11
ctcggatcct ttagatttta gtttgtcact                                        30

VECTOR FOR ANTI-HPV VACCINE AND TRANSFORMED MICROORGANISM BY THE VECTOR

CROSS-REFERENCE TO RELATED APPLICATIONS

This is a divisional filed under the provisions of 35 USC 120 of U.S. patent application Ser. No. 10/530,083 filed Apr. 1, 2005 as a U.S. national phase under 35 USC 371 of international patent application PCT/KR2003/002163 filed Oct. 17, 2003, which in turn claims priority of Korean Patent Application No. 10-2002-0063378 filed Oct. 17, 2002.

TECHNICAL FIELD

The present invention relates to a vector for expressing a vaccine against a surface antigen of papilloma virus, a microbial transformant and a vaccine using said microbial transformant or purified extract thereof.

BACKGROUND

Cell surface display is new technique by which a desired protein is expressed and attached onto a cell surface of microbe and is an application by using molecular biological information as the mechanism of protein secretion is elucidated. Precisely, the cell surface display uses a microbial cell surface protein derived from bacteria, yeast or the like as a surface anchoring motif to produce an exogenous protein on a cell surface. It has a broad range of application and thus, can be used to produce recombinant live vaccines, to prepare and screen a peptide/antigen library and to make whole cell absorbent, whole cell bioconversion catalyst and the like. Namely, this technique is considerably potential for an industrial use, since a variety of exogenous protein expressed onto a cell surface decides the scope of industrial application.

Cell surface carrier is the most important factor to express an exogenous protein onto a cell surface successfully. To select an effective anchoring motif expressing an exogenous protein onto a cell surface is essential for this technique.

Accordingly, the surface expression carrier makes ready for several features as follows: Above all, some secretion signal is essential to help an exogenous protein pass through a cell inner membrane and finally arrive at a cell surface. Second, a targeting signal is required to anchor an exogenous protein stably onto a cell outer surface. Third, an anchoring motif seldom affects a cell growth even if massively expressed onto a cell surface. Fourth, an exogenous protein sustains the 3-dimensional structure to be expressed stably, regardless of a protein size. However, a surface expression carrier satisfying all the terms is not found yet and is complemented only to settle some disadvantage of above cases.

In a broad sense, the surface anchoring carrier is now classified to 4 kinds, including cell outer membrane protein, lipoprotein, secretory protein, surface organelle protein such as flagella protein. In case of Gram negative bacteria, a surface protein present on a cell outer membrane such as Lam B, Pho E (Charbit et al., J. Immunol., 139: 1658-1664, 1987; Agterberg et al., Vaccine, 8: 85-91, 1990), Omp A and the like is often exploited as a surface anchoring carrier. Besides, a lipoprotein such as Tra T (Felici et al., J. Mol. Biol., 222: 301-310, 1991), peptidoglycan associated lipoprotein (PAL) (Fuchs et al., Bio/Technology, 9: 1369-1372, 1991), Lpp (Francisco et al., Proc. Natl. Acad. Sci. USA, 489: 2713-2717, 1992) and the like has been adopted and also fimbriae protein such as Fim A or Fim H adhesin of type I fimbriae (Hedegaard et al., Gene, 85: 115-124, 1989) and pili protein such as Pap A pilu subunit have been attempted to produce an exogenous protein. Furthermore, ice nucleation protein (Jung et al., Nat. Biotechnol, 16: 576-560, 1998; Jung et al., Enzyme Microb. Technol, 22(5): 348-354, 1998); Lee et al., Nat. Biotechnol., 18: 645-648, 2000), *Klebsiella oxytoca* pullulanase (Komacker et al., Mol. Microl., 4: 1101-1109, 1990), *Neisseria* IgA protease (Klauser et al., EMBO L., 9: 1991-1999, 1990) or the like have been reported to become a surface anchoring motif. In case of Gram positive bacteria, it is known that a malaria antigen is effectively produced by using protein A derived form *Staphylococcus aureus* as a surface anchoring motif and that a surface coat protein from lactic acid bacteria is displayed well on a cell surface. Thus, the surface protein of Gram positive bacteria is verified to become a cell surface anchoring protein.

Previously, the present inventors have investigated a synthetic complex gene of poly-. γ-glutamate, pgs BCA derived from *Bacillus* sp. strain, as to whether it is applicable for new surface anchoring motif. Practically, pgs BCA gene was used to develop a novel recombinant vector expressing an exogenous protein onto a microbial surface and a method for producing an exogenous protein onto a cell surface in a large scale (Korean Patent Application No. 10-2001-48373).

Furthermore, the surface expression carriers described above have been tried a lot to produce various pathogenic antigens or antigenic determinants stably through the genetic engineering technique on a highly productive bacterial surface. Especially, it is reported that an exogenous immunogen can induce more consistent and stronger immune reactions when expressed onto a non-pathogenic bacterial surface and orally administered as a live vaccine, compared with typical vaccines such as detoxified pathogenic bacteria or virus.

Since the microbial surface structure acts as an adjuvant enhancing the antigenicity of exogenous protein expressed onto a cell surface, the immune reaction is known to be induced by live bacteria within a body. It is a remarkable event to develop a recombinant live vaccine of non-pathogenic bacterium through this surface expression system.

Human papilloma virus (hereinafter, referred to as "HPV") is presumed to world-widely infect more than 50% of all adult people. Especially, 4 types of HPV including HPV 16, 18, 31 and 45 are confirmed to cause a cervical cancer to more than 80% (Lowry D. R., Kirnbauer R., Schiller J. T., Proc. Natl. Acad. Sci., 91: 2436-2440, 1994). Papilloma virus is highly species-specific and small DNA tumor virus and belongs to family Papovaviridae which is infected to mammals such as human, cow, rabbit, sheep and so on and provokes a wart or papilloma on skin or mucosa (Pfister H., Adv. Cancer Res. 48: 113-147, 1987). Among these species, HPV are known to approximately 70 types and from more than 20 types cause tumors on skin mucosa of oral cavity or genital organs. Precisely, HPV 16 (type) and HPV 18 are reported to cause cervical cancer mostly covering women cancers.

Cervical cancer is found frequently in women, next to breast cancer world-widely. WHO (World Health Organization) has reported that cervical cancer occurring newly is over 5 hundred thousand cases every year and more than 3 hundred thousand of patients are died from cervical cancer every year in the world. Especially in the developing country, cervical cancer is a major cause of women death (Pisani P., Parkin D. M., Ferlay J., Int. J. Cancer 55: 891-903, 1993). IARC statistics showed that the most effective way to eradicate papilloma virus infection is to administer a preventive vaccine for the future, since the developing country has even more chronic patients than the advanced country.

In order to develop certain vaccine against virus, the animal culture system should be equipped properly and exploited to produce and purify virus particles in a large scale. However, HPV is hardly changed to a virus particle in vitro or in vivo, since the virion is formed only in a fully differentiated keratinocyte. Thus, there are severe problems to develop vaccines against cervical cancer for the prevention and the treatment as well as to produce virus enough for this researches. In a broad sense, 2 types of vaccine including prophylactic vaccine and therapeutic vaccine are focused as a method for producing vaccines against cervical cancer. For a purpose, the prophylactic vaccine generates a stronger neutralizing antibody by HPV L1/L2 antigen and thus prevents a host from HPV infection. Even if already infected, it makes the disease no more progressed. In the meantime, the therapeutic vaccine uses HPV E6/E7, induces specific cellular immune reactions and degenerates lesions or malignant tumor.

As searched out for last 20 years, HPV infected to human epithelium has various kinds of genotype and is associated with several benign and malignant tumors. Such an experimental data and discovery as to HPV promotes to develop HPV vaccine. HPV recombinant virus like particle is assumed more optimistic among several HPV vaccine candidates since better for an immune reaction than any other viruses except papilloma virus, through vaccine efficacy experiments in animal model and human (Koutsky L. A., Ault K. A., Wheeler C. M., Brown D. R., Barr E., Alvarez F. B., Chiacchierini L. M., Jansen K. U., N. Engi. J. of Med. 347 (21): 1645-1651, 2002). Furthermore, HPV infection is confirmed recently to be the most essential cause of cancer definitely and scientists become interested in HPV studies and directly participate in this so as to accelerate the development of HPV vaccines globally. Nowadays, HPV vaccines widely known exploits HPV recombinant protein, HPV recombinant virus like particle, HPV DNA and the like to manufacture products.

In bacteria, yeast, animal cell and so on, the recombinant protein produced from some HPV partial composition through the recombinant DNA technology and a synthetic peptide in which some major epitope is synthesized chemically are tried to develop vaccines. Generally, recombinant proteins are produced through a common system such as bacteria, yeast, baculovirus, recombinant vaccinia virus and the like, by which several researches are accomplished to produce HPV recombinant proteins and to identify the antibody forming ability against HPV in serum, the induction of cellular immune reaction and the like. However, the virus system using animal and insect cells is disadvantageous and thus contaminated during cultivation and hard to be purified. Including the synthetic peptide, overall cases cost high and are commercially limited in the industry, since papilloma virus infected patients are often found in the developing countries.

Practically, HPV L1 virus like particle (hereinafter, referred to as "VLP") has been disclosed to be produced as a live recombinant vaccinia virus through a mammary gland cell culture (Hagensee, M. E., Yaegashi, N., Gallowat, D. A., J. Virol. 67: 315-322, 1993) and VLP has been reported to generate neutralizing antibodies in a mouse model system (Schiller J. T., Lowry, D. R., Seminars in Cancer Biol. 7: 373-382, 1996). The therapeutic vaccine has been exploited by using HPV E6 and E7 protein uniquely expressed in cervical cancer (Bubenik J., Neoplasma 49: 285-289, 2002). In addition, HPV E6/E7 protein has been searched out as an immune target to treat cervical cancer and to develop a therapeutic vaccine, since it is a cancer specific antigen and associated with the cancerization of HPV infected cells. Actually, it is demonstrated that when HPV E6/E7 protein produced by the microbial system is administered to tumor cell-injected mice, the tumor formation is prevented and delayed (Gao L., Chain B., Sinclair C., J. Gen. Virol. 75: 157-164, 1994; Meneguzzi G., Cern C., Kieny M. P., Virology 181: 62-69, 1991). As shown in other cases, live virus vaccine has also problems to provoke an viral proliferation excessively and is liable to stay in a research level. Unfortunately, it takes a long time to be commercialized and also needs considerable clinical trials. In order to overcome such a disadvantage, virus vectors which are inhibited or deficient in the replication are explored but not commercialized yet (Moss B., Proc. Natl. Acad. Sci. USA 93: 11341-11348, 1996).

On the other hand, vaccine studies by using bacterial vectors are proceeded actively. It is disclosed that HPV 16 VLP produced from attenuated *Salmonella typhimurium* inducibly generate antigen specific antibodies in mouse mucous membrane or whole body. Besides, vaccine composed of synthetic peptides uses only essential synthetic epitope enough to induce an immune reaction for the vaccination and particularly, an epitope inducing cytotoxic T lymphocyte (CTL) against HPV 16 E6/E7 has been already elucidated (Ressing M. E., Sette A., Brandt R. M., J. Immunol. 154: 5934-5943, 1995).

In addition to such a trials, vegetables including tomatoes, potatoes and so on are utilized to produce viral antigens in plants and also a vegetable transformant itself is being attempted toward oral vaccine or edible vaccine. As a model case, hepatitis B surface antigen particle (Thavala Y. F. and C. J. Artzen. Proc. Natl. Acd. Sci. USA 92: 3358-3361) and capsid protein L1 and L2 of papilloma virus (Korean Patent Application 10-2000-0007022) are exemplified. In the plant system, however, HPV L1 protein is expressed in so small amount and so hard for the purification to limitedly engaged in commerce.

Therefore, since human papilloma virus is considered to be very often infected to people in the developing countries, in order to prevent and effectively treat tumors derived from papilloma virus onto skin mucus of oral cavity or genital organs, it is deeply required to develop a novel method for preparing human papilloma viral antigens more economically and stably.

DISCLOSURE OF THE INVENTION

In order to settle above-mentioned technical problems, the object of the present invention is to provide a recombinant vector and a microbial transformant which can produce HPV antigen through a microbial surface expression system.

In addition, another object of the present invention is to provide a vaccine for treating and preventing mucosal tumor which is comprised of a microbial transformant in which HPV antigen is expressed onto a cell surface, a crude HPV antigen extracted from the transformant or a HPV antigen purified from the microbial transformant as an effective component.

In order to attain the above-mentioned object, the present invention provides a surface expression vector for preparing a vaccine which contains one or more than two genes encoding poly-γ-glutamate synthetase complex selected among pgs B, pgs C and pgs A and a surface antigen protein gene from human papilloma virus (HPV).

The gene pgs B, pgs C and pgs A mentioned in the present invention include nucleotide sequences comprising SEQ ID NO. 1, SEQ ID NO. 2 and SEQ ID NO. 3 respectively.

The surface antigen protein gene of the present invention can be any kind of gene encoding a HPV surface component protein. For example, a capsid protein of human papilloma virus, HPV L1 or HPV L2 antigen protein gene can be used solely or more than two genes, coordinately. The major capsid, HPV L1 antigen protein gene is preferable to be used.

The tumor-associated antigen gene of the present invention can be any kind of gene encoding a tumor-associated protein of HPV and a tumor-associated antigen protein of human papilloma virus, HPV E6 or HPV E7 antigen protein gene can be used solely or more than two genes can be used coordinately. Besides, the modified tumor-associated gene E6 and E7 can be used as an antigen and the major tumor-associated antigen protein of HPV, E7 antigen protein is preferable to be used.

More preferably, the gene encoding poly-.γ-glutamate synthetase complex of the present invention can be pgs A.

Furthermore, the present invention relates to a microbial transformant transformed with the recombinant vector for preparing a vaccine described above.

Any kind of microorganism can be applied for the present invention, if non-toxic to a living body or attenuated. For example, *Escherichia coli, Salmonella typhi, Salmonella typhimurium, Vibrio cholera, Mycobacterium bovis, Shigella* and the like can be selected as Gram negative bacterium and *Bacillus, Lactobacillus, Lactococcus, Staphylococcus, Lysteria monocytogenesis, Streptococcus* and the like as Gram positive bacterium properly.

The present invention provides various vaccines for treating and preventing mucosal tumors which exploits microbial transformant itself expressing an antigen protein onto a cell surface, or uses crude extract of cell membrane components after microbes are disrupted, or exploits an antigen protein purified from a microbes as an effective component. That is to say, the vaccine of the present invention can be used for a therapeutic drug or a prophylactic drug for treating or preventing a tumor which is caused by HPV and occurs on the mucosal membrane of oral cavity or genital organs, especially women cervical cancer.

The vaccine of the present invention can be administered orally or be edible, and injected hypodermically or peritoneally and can be a washing solution for genital organs. When administered directly to women genital organ, a host cell can be preferably selected from useful bacteria such as *Lactobacillus* sp. strain, which is clear to those skilled in this art.

Besides, the vaccine of the present invention can be sprayed for the nasal cavity.

The mucus immunization is very important to prevent HPV infection since the HPV infection is often caused onto the mucosal surface. The oral vaccine using a microbial transformant itself is expected to be more effective to prevent HPV than the parental vaccine, since a microbe expressing HPV antigen onto a cell surface is advantageous to induce a mucosal response on the membrane more efficiently.

Concretely, the present invention provides the recombinant vector for a vaccine use, pHCE2LB:pgsA-HPV L1 (See FIG. 1) which contains pgs A gene, a poly-.γ-glutamate synthetase complex gene derived from *Bacillus* sp. strain and expresses HPV L1 protein, a fused protein connecting the C-terminus of pgs A and the N-terminus of HPV L1 onto a cell surface of Gram negative bacterium or Gram positive bacterium and also the microbial transformant for the surface expression. The *Escherichia coli* transformant transformed with the above-mentioned vector for a vaccine use has been deposited separately (accession number: KCTC 10349 BP).

In addition, the present invention provides the surface expression recombinant vector for a vaccine use, pHCE2LB:pgsBCA-HPV E7 (See FIG. 5) which contains pgs BCA gene, a poly-.γ-glutamate synthetase complex gene derived from *Bacillus* sp. strain and expresses HPV E7 protein, a fused protein connecting the C-terminus of pgs A and the N-erminus of HPV E7 onto a cell surface of Gram negative bacterium or Gram positive bacterium and also the microbial transformant for the surface expression. The *Escherichia coli* transformant transformed with the above-mentioned vector for a vaccine use has been deposited separately (accession number: KCTC 10520 BP).

BRIEF DESCRIPTION OF THE DRAWINGS

The above and other objects, features and other advantages of the present invention will be more clearly understood from the following detailed description taken in conjunction with the accompanying drawings, in which.

EXAMPLES

Figure 1:
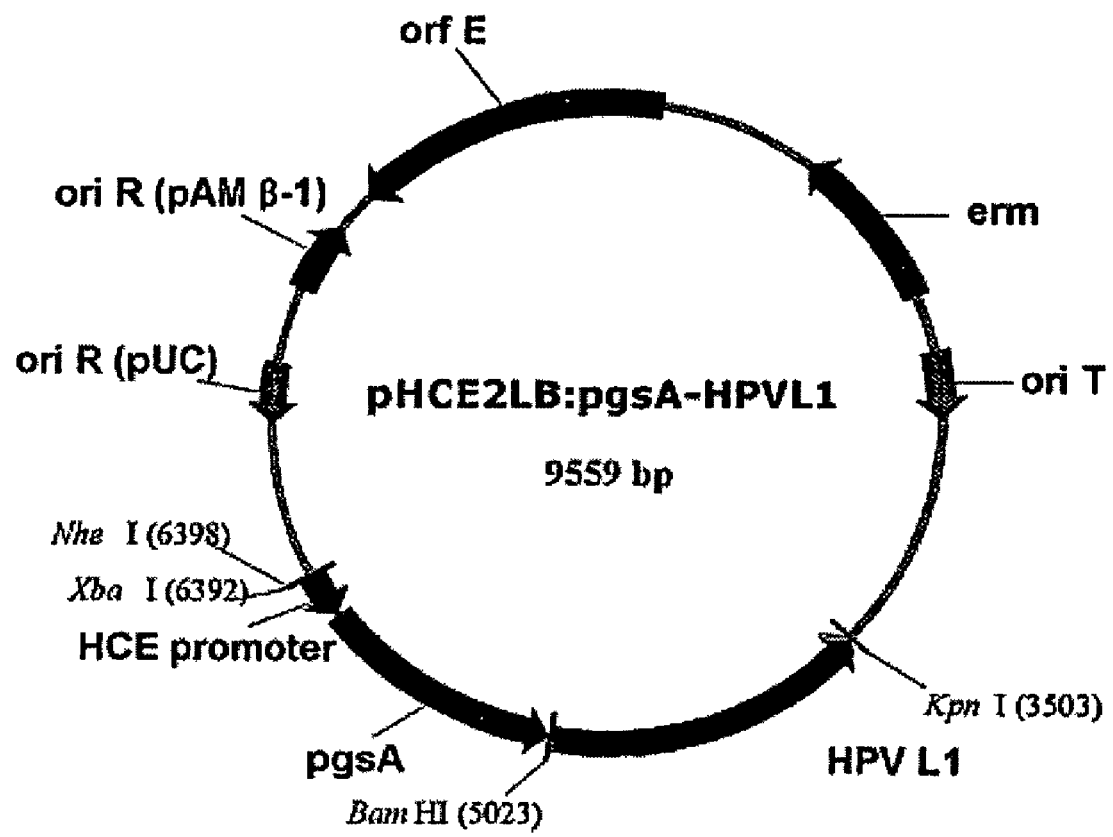
FIG. 1 depicts the genetic map of the recombinant vector pHCE2LB:pgsA-HPV L1 which uses Gram negative bacterium and Gram positive bacterium as a host cell for the surface expression.

Practical and presently preferred embodiments of the present invention are illustrated as shown in the following Examples.

However, it will be appreciated that those skilled in the art, on consideration of this disclosure, may make modifications and improvements within the spirit and scope of the present invention.

Especially, HPV type 16 L1 antigen protein gene is adopted in following Examples, but any kind of antigen protein gene, a HPV capsid protein gene such as L1, L2 or so on from any other types of HPV strains can be used solely or more than two coordinately. In following Examples, HPV type 16 E7 gene, a major antigen protein gene associated with a cancer induction is used but any other cancer inducing antigen protein gene of other HPV strains can be selected solely or coordinately.

Besides in following Examples, the cell outer membrane protein gene, pgs BCA participating in the poly-.γ-glutamate synthesis is collected from *Bacillus* subtilis var. chungkookjang (accession number: KCTC 0697 BP), but the vector including all the kinds of pgs BCA gene from *Bacillus* sp. strain producing poly-.γ-glutamate, microbial transformants using the vector or the like can be within the scope of the present invention. Precisely, other pgs BCA genes having more than 80% homology of sequences present in the pgs BCA of Bacillis subtilis chungkookjang and derived from other microbial strains can be used to construct the vector for a vaccine use, which may be within the scope of the present invention.

As demonstrated in following Examples and Indirect Examples, pgs BCA gene can be utilized all or partially to construct the vector for a vaccine use, which may be within the scope of the present invention.

Furthermore in following Examples, *Salmonella typhi* as Gram negative bacterium and *Lactobacillus* as Gram positive bacterium are used as a host cell for the above-mentioned vector, but in addition to these bacteria, other Gram positive or Gram negative bacteria can be used for the same result, which is clear to those skilled in this art.

Also in following Examples, the microbial transformant itself transformed with the vector for a vaccine use is only disclosed to apply for a living body as a live vaccine. However, according to general information in vaccine associated technical fields, it is natural to obtain the same or similar results even if crude extract from the above microbial transformant or purified proteins are administered into a living body.

Example 1

Construction of the Recombinant Vector pHCE2LB : pgsA: HPV L1 for the Surface Expression Cell outer membrane protein derived from *Bacillus* sp. strain and participating in the synthesis of poly-.γ-glutamate is exploited. Among the cell outer membrane gene, pgsBCA, gene pgsA was used to prepare the recombinant vector pHCE2LB:pgsA-HPV L1 which can express the major capsid protein L1 of human papilloma virus Type 16 (hereinafter, referred to as "HPV") onto a cell surface by using Gram negative bacteria and Gram positive bacteria as a host cell.

Above all, the gene encoding HPV L1 is introduced into the surface expression vector pGNA which uses Gram negative bacteria as a host cell (obtained from an applicant of Korean Patent Application No. 10-2001-48373). Precisely, approximately 1.5 kb of human papilloma virus gene cloned in pUC19 was utilized as a template and oligonucleotides encoding HPV L1 and containing the nucleotide sequence of SEQ ID. NO. 4 or SEQ ID. NO. 5 as a template and then the polymerase chain reaction was performed. As a result, 1518 bp-sized gene was amplified.

The primers of SEQ ID. NO. 4 and SEQ ID. NO. 5 were made to include the recognition site of restriction enzyme Bam HI and Hind III present in the cloning vector pGNA for the surface expression. The HPA L1 antigen gene amplified above was digested with the restriction enzyme Bam HI and Hind III and ligated and adjusted in translation codons to the C-terminal region of cell outer membrane protein gene pgsA which participates in the synthesis of poly-.γ-glutamate and is derived from the cloning vector pGNA so as to manufacture the recombinant vector pGNA-HPV L1.

In order to obtain the DNA fragment containing HCE promoter, pgsA and HPV L1 from the recombinant vector prepared above, the recombinant vector pGNA-HPV L1 was digested with the restriction enzyme Nhe I and Sca I and the resulting fragment was inserted to the restriction enzyme Xba I and Sma I site within a multi-cloning site of common cloning vector pAT19 for Gram positive bacteria so as to construct the recombinant vector pHCE2LB:pgsA-HPV L1 (See FIG. 1).

The recombinant vector for the surface expression in the present invention was transformed to *Escherichia coli* and the bacterial transformant including pHCE2LB:pgsA-HPV L1 was deposited on Oct. 4, 2002 to Korea Research Institute of Bioscience and Biotechnology, Gene Bank (KCTC, 52 Oundong, Yusong-ku, Taejon 305-333, Republic of Korea) with the accession number KCTC 10349 BP.

Example 2

Surface Expression of HPV L1 Fused with pgsA

Figure 2:
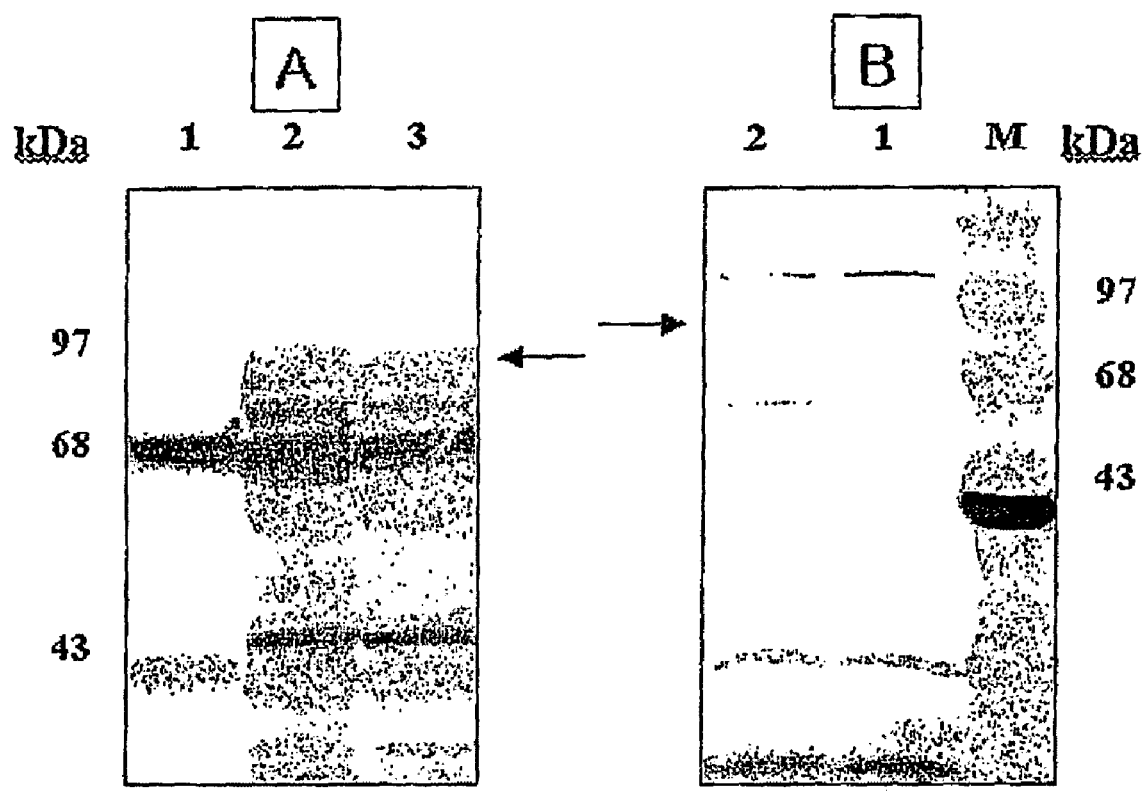
FIGS. 2A and 2B depicts the expression of HPV L1 antigen fused with pgs A within *Salmonella* strain and *Lactobacillus* strain transformed with the recombinant vector pHCE2LB:pgsA-HPV L1 for the surface expression.

Gram negative bacterium *Salmonella typhi* Ty21a was transformed with the recombinant vector pHCE21LB:pgsA-HPV L1 for the surface expression described above and examined the protein expression of HPV L1 antigen fused with pgsA in *Salmonella typhi* Ty21a. Then, Gram positive bacterium *Lactobacillus* was transformed, identified the presence of the recombinant vector pHCE21LB:pgsA-HPV L1 within *Lactobacillus* strain and examined the protein expression of HPV L1 antigen fused with pgsA (See FIG. 2). The bacterial expression of HPV L1 antigen associated with the C-terminus of pgsA gene participating in the synthesis of poly-.γ-glutamate was examined by performing SDS-polyacrylamide gel electrophoresis and western blotting with specific antibodies against HPV L1.

Concretely, *Salmonella typhi* Ty21a transformed with the recombinant vector pHCE2LB:pgsA-HPV L1 was cultured onto 500 mL flask including 50 mL of LB medium (yeast extract 5 g/L, tryptone 10 g/L, salt 5 g/L, pH 7.0) containing 100 mg/L of antibiotic (erythromycin) and induced for the surface expression. In addition, *Lactobacillus casei* was transformed with the recombinant vector pHCE2LB:pgsA-HPV L1, cultured onto MRS medium (*Lactobacillus* MRS, Becton Dickinson and Company Sparks, USA) at 37.degree. C. in static culture, proliferated and induced for the surface expression.

Afterward, *Salmonella typhi* Ty21a and *Lactobacillus casei* were induced for the surface expression and proteins were obtained in the same cell density, and denatured for sample uses. Then the proteins were analyzed through SDS-polyacrylamide gel electrophoresis and in a fractionated state, transferred onto PVDF membrane (polyvinylidene-difluoride membrane: Bio-Rad). The resulting PVDF membrane was submerged in a blocking buffer (50 mM Tris-HCL, 5% skim milk, pH 8.0), shaked for 1 hour to be blocked, and reacted for 12 hours with a monoclonal primary antibody against HPV L1 proteins which was derived from mouse and diluted to 1,000 fold in the blocking buffer. The completely reacted membrane was washed with the buffer and reacted for 4 hours with a mouse secondary antibody which was conjugated with biotins and diluted to 1,000 fold in the blocking buffer. Then, the resulting membrane was washed with the buffer, reacted with avidin-biotin reagent for 1 hour and washed again. The washed membrane became chromophored by adding H.sub.2O.sub.2 and DAB solution and was identified to have a specific binding between specific antibody against HPV L1 and the above fused protein. (See FIG. 2)

In FIG. 2A, lane 1 is *Salmonella typhi* Ty21a, host cell not transformed and lane 2, 3 is *Salmonella typhi* Ty21a transformed with the recombinant vector pHCE2LB:pgsA-HPV L1. In FIG. 2B, lane 1 is *Lactobacillus casei* not transformed and lane 2 is *Lactobacillus casei* transformed with the recombinant vector pHCE2LB:pgsA-HPV L1. As illustrated in Figs, the fused protein expressed from the recombinant vector pHCE21LB:pgsA-HPV L1 was verified at 97.4 Kda band. Since pgsA has about 41.8 KDa and L1 protein, about 55.6 Kda, the band having above 97.4 Kda is elucidated as a fused protein of pgsA and L1 protein.

Example 3

Induction of Immune Reaction in *Lactobacillus* Expressing HPV L1 Antigen Onto Cell Surface The recombinant vector pHCE2LB:pgsA-HPV L1 for the surface expression was transformed to Gram positive bacterium, *Lactobacillus casei*, induced to express the antigen onto cell surface of *Lactobacillus casei* as described in Example 2 and then the cell outer membrane protein pgsA participating in the synthesis of poly-.γ-glutamate and the HPV 16 fused with L1 antigen were examined for the antigenicity.

Concretely, the recombinant vector pHCE2LB:pgsA-HPV L1 of the present invention was transformed to *Lactobacillus casei* for the surface expression, harvested to adjust each cell to the same concentration and washed several times with PBS buffer (pH 7.4). Then, *Lactobacillus* in which HPV16 L1 antigen is expressed onto cell surface and *Lactobacillus* not transformed were administered in 5.times.10.sup.10 bacteria to an oral cavity of 4.about.6 week BALB/c mouse, three times every other day in the first week and the second week and injected additionally after 2 weeks, three times every other day. As a standard group, mice which were administered with HPV 16 L1 virus like particle (VLP) expressed from yeast twice every other day were used.

In a 2-week interval after orally administered and venous injected, mice were victimized. Then, sera of each mouse group were collected to measure IgG antibody titers against HPV 16 L1 antigen within serum and suspension solutions washing internal organs, bronchial tube, lung and vagina were tried to estimate IgA antibody titers against HPV 16 L1 antigen by using ELISA method (Enzyme-linked immunosorbent assay) (See FIG. 3a, 3b). For the ELISA method calculating IgG and IgA antibody titers against HPV 16 L1 antigen, HPV 16 L1 virus like particle (VLP) expressed from yeast was used as an antigen. Precisely, for measuring IgG antibody titer, horseradish peroxidase conjugated anti-mouse IgG and for calculating IgG antibody titer, horseradish peroxidase conjugated anti-mouse IgA were utilized.

Figure 3A:
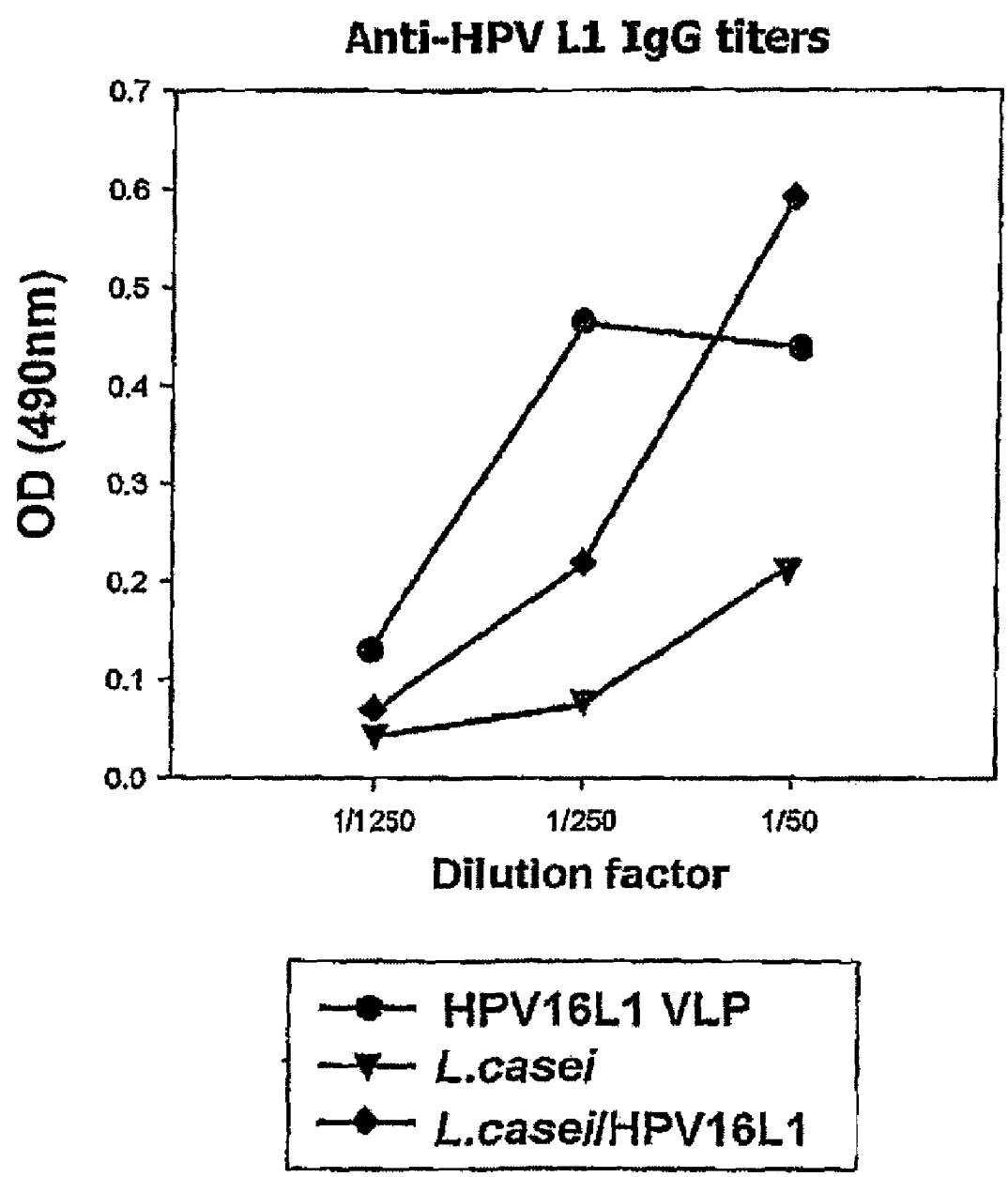
FIG. 3A depicts the IgG antibody titer against HPV L1 antigen in serum from mouse in which *Lactobacillus casei* transformed with the recombinant vector pHCE2LB:pgsA-HPV L1 of the present invention and then verified to express the antigenic determinant onto a cell surface, is orally administered in a proper amount for some time.
Figure 3B:
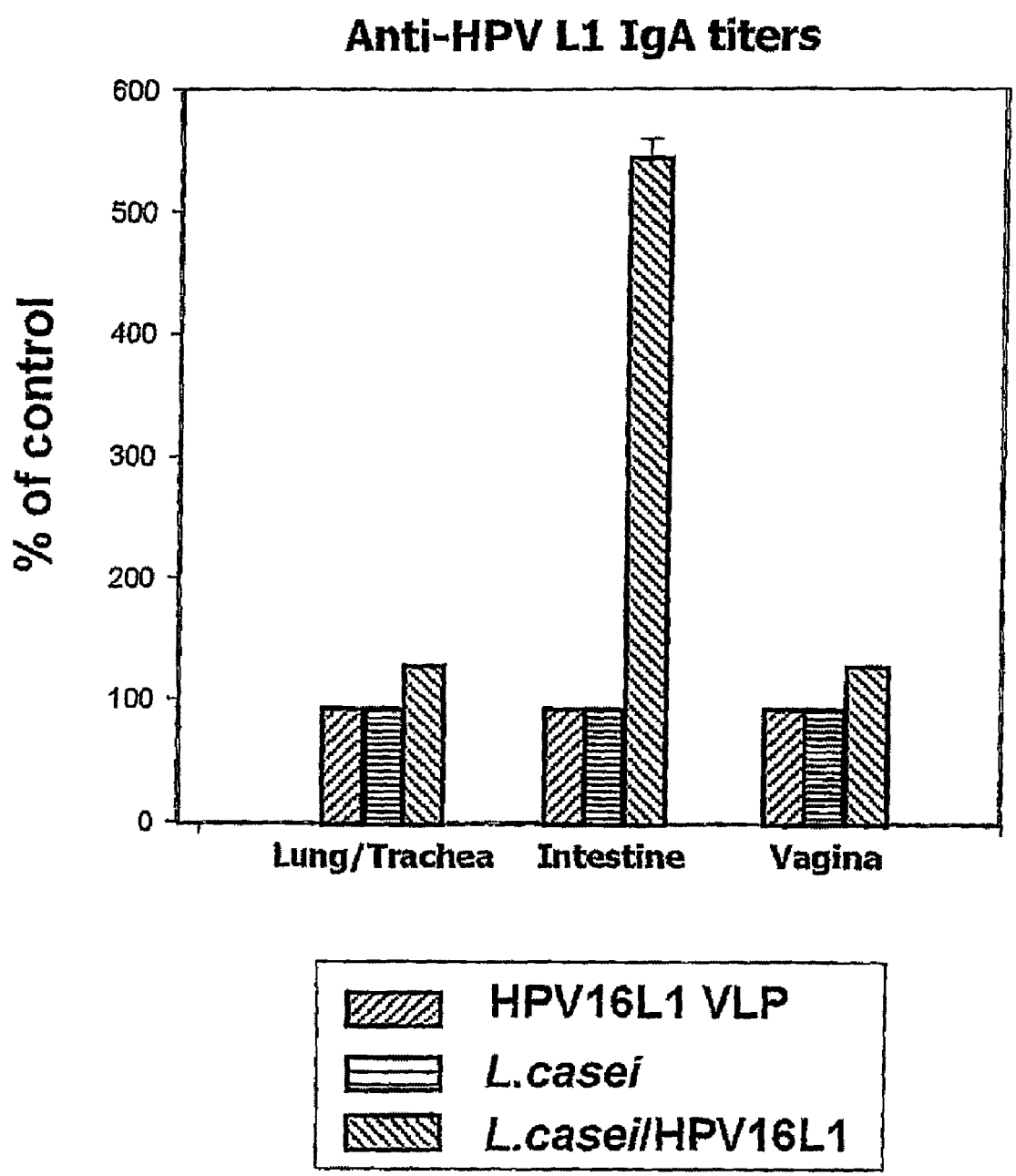
FIG. 3B depicts the IgG antibody titer against HPV L1 antigen in mouse washing solution of intestine, bronchial tube, lung and vagina to which *Lactobacillus casei* transformed with the recombinant vector pHCE2LB:pgsA-HPV L1 and then verified to express the antigenic determinant onto a cell surface, is orally administered in a proper amount for some time.

In FIG. 3a, ( ) is a group not transformed and orally administered with *Lactobacillus casei*; ( ) a group intravenously injected with L1 virus like particle of HPV 16 (VLP); and ( ) a group orally administered with *Lactobacillus casei* transformed with the vector pHCE2LB:pgsA:HPV. In FIG. 3b, is a group not transformed and orally administered with *Lactobacillus casei*; a group intravenously injected with L1 virus like particle of HPV 16 (VLP); and a group orally administered with *Lactobacillus casei* transformed with the vector pHCE2LB:pgsA:HPV.

Consequently as illustrated in FIG. 3a, the serum solution which was obtained from BALB/c mouse group administered with *Lactobacillus casei* transformed with the vector pHCE2LB:pgsA-HPV L1 and diluted was confirmed to have a considerably higher IgG antibody titer against human HPV L1 antigen than that of a standard BALB/c mouse group, and to increase the antibody titers, which can be compared with those of a group intravenously administered with HPV 16 L1 virus like particle (VLP).

As illustrated in FIG. 3b, the suspension solution which washed internal organs, bronchial tube, lung, the internal part of vagina or the like of BALB/c mouse group administered with *Lactobacillus casei* transformed with the vector pHCE2LB:pgsA-HPV L1 and diluted, was confirmed to increase IgG antibody titer against human HPV L1 antigen, which can be compared with those of the standard group intravenously administered with HPV 16 L1 virus like particle (VLP). Especially, the suspension of internal organ had the more remarkable IgA antibody titer against HPV 16 L1 antigen.

Accordingly, the microbial transformant of the present invention was verified to produce IgG antibody against HPV as an index of whole body immune induction and also IgA antibody against HPV as an index of limited immune, mucose immune induction and thus, the microbial transformant can be applied for a live vaccine.

Example 4

Cytolysis Activity of Spleen Cell from Experimental Animal Immunized with *Lactobacillus* Expressing HPV L1 Antigen Onto Cell Surface In order to investigate whether a cell-mediated immune reaction is also induced among immune reactions through the same process, splenocytes were separated from the experimental mice immunized with *Lactobacillus* expressing HPV L1 antigen onto a cell surface and measured as to the activity of cytotoxic lymphocyte (CTL).

Concretely, the splenocyte of Balb/c mouse not immunized and 10.mu.g of synthetic HPV 16 L1 peptide were incubated together at 37.degree. C. for 3 hours and irradiated with 4,000 rad so as to prepare stimulating cells.

As described in Example 3, the splenocytes of Balb/c mice immunized with *Lactobacillus* expressing HPV L1 antigen onto a cell surface were separated, mixed with a stimulating cell in which a synthetic peptide was loaded and cultivated for 6 days so as to prepare an effector cell. At this moment, the cell ratio of stimulating cell and effector cell was adjusted to 2:1 and additionally stimulated in 6 days. Before one day for an assay, cells used for a target cell were incubated by adding 10.mu.g of synthetic HPV 16 L1 peptide. For the day of assay, .sup.51 CrO.sub.4 was added to peptide-loaded target cell in 100.mu.Ci/10.sup.6 cell, incubated for 2 hours and washed. The effector cell prepared was allotted to a 96 well plate in a ratio to 5,000 cells/well target cell for the range of 1:100.about.1:25. The target cell and the effector cell were mixed and incubated at 37.degree. C. for 4 hours. After 4 hours, supernatant was collected to measure the release of .sup.51CrO.sub.4. The maximum release was at the point that 1% Triton X-100 and target cells were blended and the spontaneous release at the point that media and target cells were mixed and then the specific lysis was converted according to a following formula.

[Specific lysis=100*(experimental *cpm*–spontaneous *cpm*)/maximum *cpm*–spontaneous *cpm*]

Figure 4:
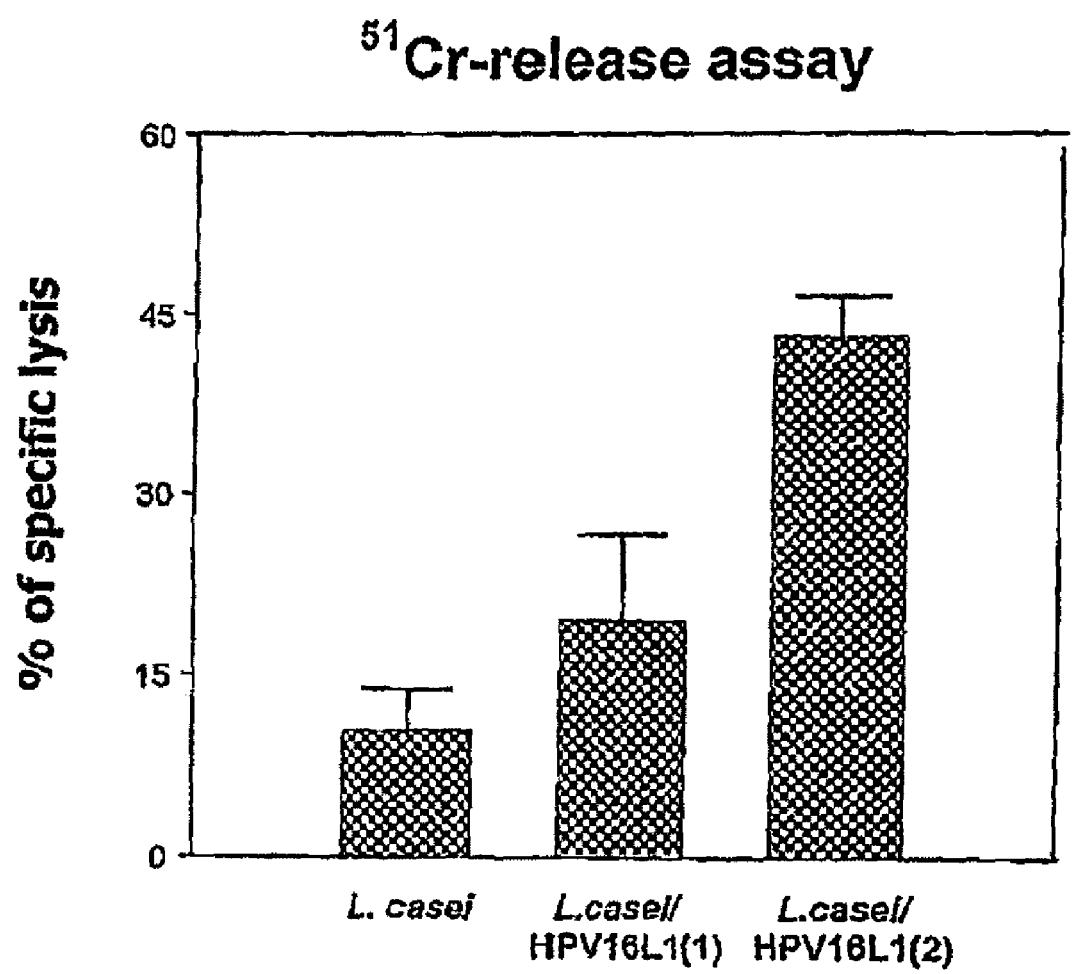
FIG. 4 depicts the cytolysis activity of cytotoxic T lymphocyte in a spleen cell obtained from mouse in which *Lactobacillus casei* transformed with the recombinant vector pHCE2LB:pgsA-HPV L1 and then verified to express the antigenic determinant onto a cell surface, is orally administered in a proper amount for some time.

The converted result of cytolysis activity was illustrated in FIG. 4.

Consequently as depicted in FIG. 4, the splenocyte of Balb/c mouse which was administered with *Lactobacillus casei* transformed with the recombinant vector pHCE2LB: pgsA-HPV L1 was identified to have a higher ratio of specific cytolysis than that of Balb/c mouse which was administered with *Lactobacillus* not transformed.

Therefore, the immune reaction induced by *Lactobacillus* expressing HPV 16 L1 antigen of the present invention was verified to be a cell-mediated immune reaction which activates a cytotoxic lymphocyte as a major effect of an oral vaccine.

Example 5

Construction of the Recombinant Vector pHCE2 LB:pgsBCA:HPV E7 for the Surface Expression The cell outer membrane protein derived from *Bacillus* sp. strain and participating in the synthesis of poly-.γ-glutamate is exploited. Among the cell outer membrane gene, pgs BCA gene was used to prepare the recombinant vector pHCE2LB: pgsA-HPV-E7 which can express the major antigen protein associated with a cancer induction E7 of HPV 16 onto a cell surface by using Gram negative bacteria and Gram positive bacteria as a host cell.

Above all, the gene encoding HPV 16 E7 is introduced into the surface expression vector pGNBCA which uses Gram negative bacteria as a host cell (obtained from an applicant of Korean Patent Application No. 10-2001-48373). Precisely, approximately 324 bp of human papilloma virus gene cloned in pUC19 was utilized as a template and oligonucleotides encoding HPV 16 E7 and containing the nucleotide sequence of SEQ ID. NO. 6 or SEQ ID. NO. 7 as a template and then the polymerase chain reaction was performed. As a result, 324 bp-sized gene was amplified.

The primers of SEQ ID. NO. 6 and SEQ ID. NO. 7 were made to include the recognition sites of restriction enzyme Bam HI and HindIII present in the cloning vector pGNBCA for the surface expression. The HPV E7 antigen gene amplified above was digested with the restriction enzyme Bam HI and HindIII and ligated and adjusted in translation codons to the C-terminal region of cell outer membrane protein gene pgsA which participates in the synthesis of poly-.γ-glutamate and is derived from the cloning vector pGNBCA so as to manufacture the recombinant vector pGNBCA-HPV E7.

Figure 5:
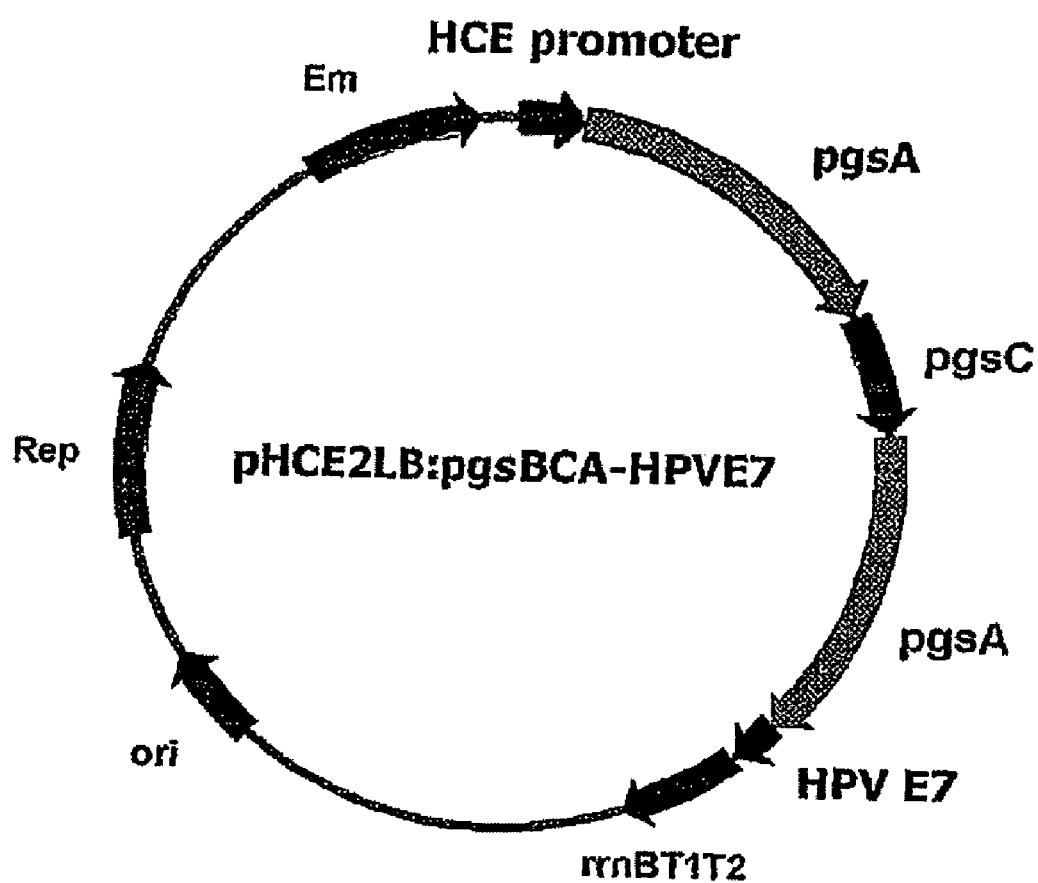
FIG. 5 depicts the genetic map of the recombinant vector pHCE2LB:pgsBCA-HPV E7 for the surface expression which uses Gram negative bacterium and Gram positive bacterium as a host cell.

In order to obtain the DNA fragment containing HCE promoter, pgsBCA and HPV E7 from the recombinant vector pGNBCA-HPV E7 prepared above, the recombinant vector was digested with the restriction enzyme Nhe I and Sca I and the resulting fragment was inserted to the restriction enzyme XbaI and Sma I site within the multi-cloning site of common cloning vector pAT19 for Gram positive bacteria so as to construct the recombinant vector pHCE2LB:pgsBCA-HPVE7 (See FIG. 5).

The recombinant vector for the surface expression in the present invention was transformed to *Escherichia coli* and the bacterial transformant including pHCE2LB:pgsBCA-HPVE7 was deposited on Oct. 7, 2003 to Korea Research Institute of Bioscience and Biotechnology Gene Bank (KCTC, 52 Oun-dong, Yusong-ku, Taejon 305-333, Republic of Korea) with the accession number KCTC 10520 BP.

Example 6

Surface Expression of HPV E7 Fused with pgsA

Figure 6:
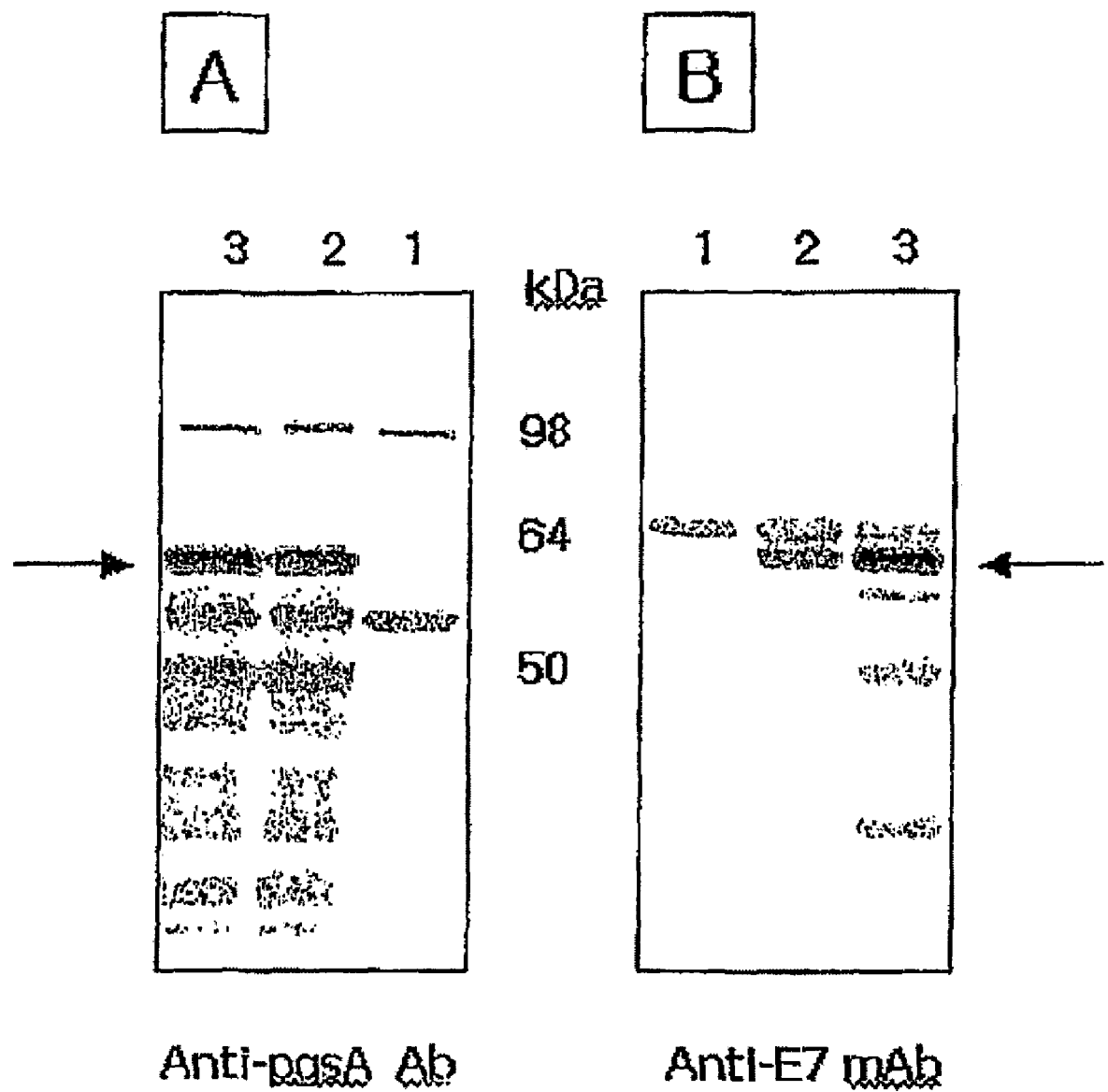
FIG. 6 depicts the expression of HPV E7 antigen fused with pgs A in *Lactobacillus* strain which is transformed with the recombinant vector pHCE2LB:pgsBCA-HPV E7 for the surface expression, by performing western blotting with specific antibodies.

Gram negative bacterium *Lactobacillus* was transformed with the recombinant vector pHCE21LB:pgsBCA-HPV E7 for the surface expression described above, identified the presence of the recombinant vector pHCE21LB:pgsBCA-HPV E7 within *Lactobacillus* strain and examined the protein expression of HPV E7 antigen fused with pgsA (See FIG. 6).

For this purpose, the surface expression vector was transformed to *Lactobacillus* and induced through the same process described in Example 2. Then, the expression of HPV E7 antigen protein fused with the C-terminus of pgsA gene participating in the synthesis of poly-.γ-glutamate was confirmed by performing SDS-polyacrylamide gel electrophoresis and western blotting with specific antibodies against pgsA (See FIG. 6A) and HPV E7 (See FIG. 6B) (See FIG. 6). In FIG. 6, lane 1 is *Lactobacillus* casei not transformed; and lane 2 and 3 are *Lactobacillus* casei transformed with the recombinant vector pHCE2LB:pgsBCA-HPV E7.

As illustrated in Figs., about 60.8 Kda band of fused protein was verified from the recombinant vector pHCE2LB: pgsBCA-HPV E7. Since pgs A has about 41.8 Kda and HPV 16 E7 antigen protein has about 19 Kda typically, the above 60.8 Kda band was elucidated to a fused protein of pgs A and HPV 16 E7 antigen protein.

Example 7

Challenge of Tumor Cell to Experimental Animal Immunized with *Lactobacillus* Expressing HPV E7 Antigen onto a Cell Surface The recombinant vector pHCE21 LB:pgsBCA-HPV E7 for the surface expression was transformed to Gram positive bacterium, *Lactobacillus* casei, induced to express the above antigen onto the surface of *Lactobacillus* casei through the same process described in Example 2 and then the inhibition effect upon the tumor proliferation was examined by the immunization of HPV 16 E7 antigen fused with cell outer membrane protein, pgs A participating in the poly-.γ-glutamate synthesis.

Concretely, *Lactobacillus casei* transformed with the recombinant vector pHCE2LB:pgsBCA-HPV E7 for the surface expression and *Lactobacillus* not transformed were treated as described in Example 3 and 5.times.10.sup.10 transformants were orally administered to 4.about.6 week—C57/BL/6 mouse three times in the first week and the second week every other day and after 2 weeks, additionally injected three times every other day.

After last injected, tumor cell line TC-1 (1.times.10.sup.4/50.mu.l) expressing HPV E7 was injected subcutaneously on the left side of mouse to be challenged.

Tumor cell line TC-1 expressing HPV E7 protein is induced from the primary lung cell of C57/BL/6 mouse which is immunized and transformed with HPV 16 E6 and E7 gene and activated human c-Ha-ras gene as demonstrated in the prior art [Lin et al., Cancer Res. 56:21-26, 1996]

In 2 weeks after tumor challenged, the tumor size was measured. Three times a week every other day, the longest and the shortest length were calculated and indicated to be doubled. The data measuring the tumor size after tumor challenged were illustrated in FIG. 7.

Figure 7:
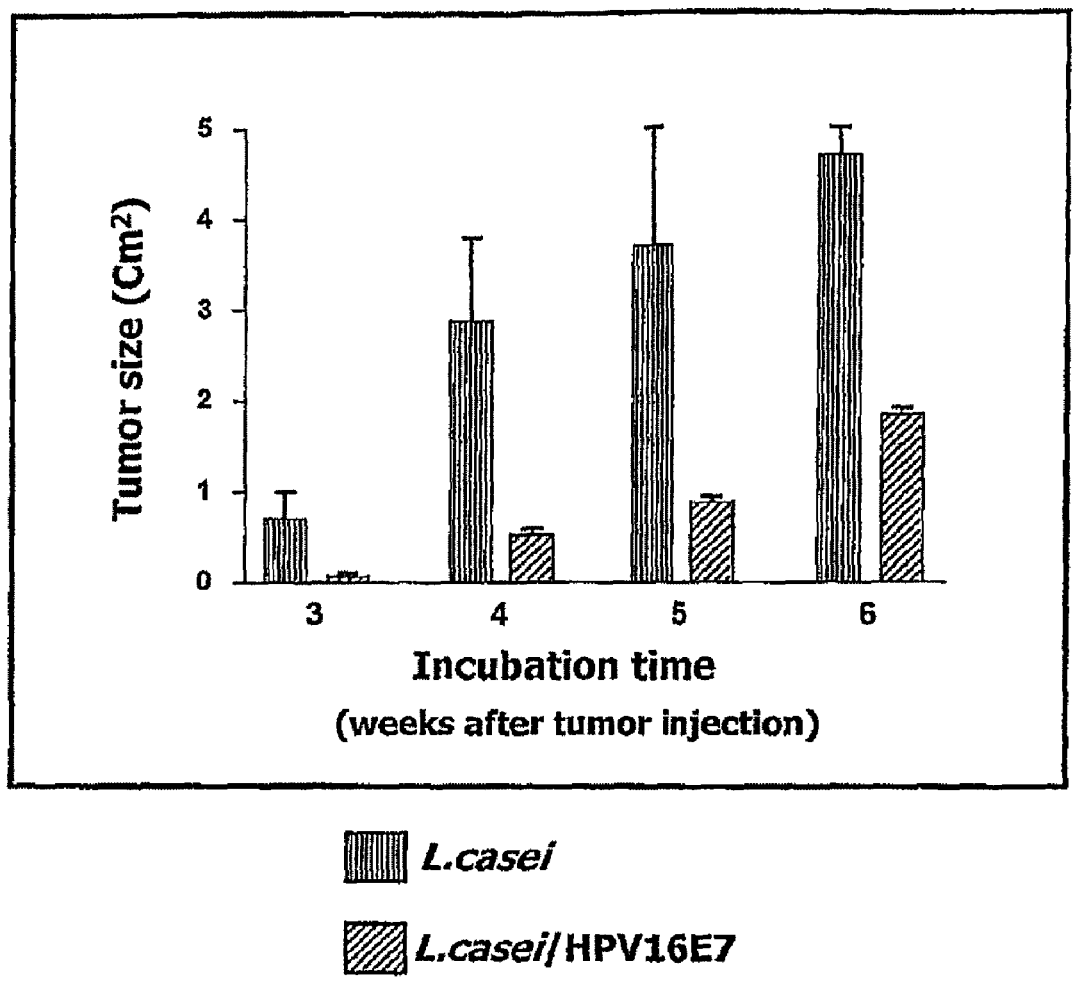
FIG. 7 depicts the proliferation rate of tumor cells obtained from mouse in which *Lactobacillus casei* transformed with the recombinant vector pHCE2LB:pgsBCA-HPV E7 and then verified to express the antigenic determinant onto a cell surface, is orally administered in a proper amount for some time and challenged according to a time lapse.

As shown in FIG. 7, tumor cell challenged with C57/BL/6 mouse which was administered with *Lactobacillus casei* transformed with the vector pHCE2LB:pgsBCA-E7 was remarkably inhibited to proliferate, compared with than the result of C57/BL6 mouse administered with *Lactobacillus* not transformed.

Therefore, it is confirmed that the immune reaction induced by *Lactobacillus* in which HPV16 E7 antigen of the present invention was expressed onto a cell surface prevent tumor cells from the proliferation.

Indirect Example

Construction of the Recombinant Vector for a Vaccine Combining pgs B, pgs C and pgs A and Experiment for Expressing Exogenous Protein onto a Cell Surface by Using the System It is confirmed that the surface expression vector can be constructed to include any one or more than two genes among pgs B, pgs C and pgs A encoding poly-.γ-glutamate synthetase complex and gene encoding exogenous protein and transformed to microbes so as to be expressed onto the microbial surface.

Accordingly, it is also identified indirectly that the vactor for a vaccine use including any one or more than two genes among pgs B, pgs C and pgs A encoding poly-.γ-glutamate synthetase complex and gene encoding HPV antigen protein of the present invention can be manufactured.

In Indirect Example, the plasmid pGNBCA and pGNCA is the same with the plasmid vector pGNpgsBCA and pGNpgsCA of the present invention respectively.

Indirect Example 1

Construction of the Recombinant Vector pGNBCA-HB168 and Surface Expression of Antigenic Determinant Forming Neutralizing Antibody of S Antigen Cell outer membrane gene, pgs BCA participating in poly-.γ-glutamate synthesis derived from *Bacillus* sp. strain was utilized to construct the recombinant vector pGNBCA-HB 168 expressing antigenic determinant forming neutralizing antibody of hepatitis B virus S antigen onto the cell surface by using Gram negative bacterium as a host cell.

In order to introduce hepatitis B virus S antigen gene to the surface expression vector pGNBCA by using Gram negative bacterium as a host cell, approximately 1.4 kb of hepatitis B virus gene cloned in the common cloning vector pUC8 was used as a template and oligonucleotides containing the nucleotide sequences of SEQ ID NO. 8 and SEQ ID NO. 9 as a primer. Then S antigen gene was amplified by performing the polymerase chain reaction. At this moment, the amplified gene is 168 bp in the size.

Figure 8:
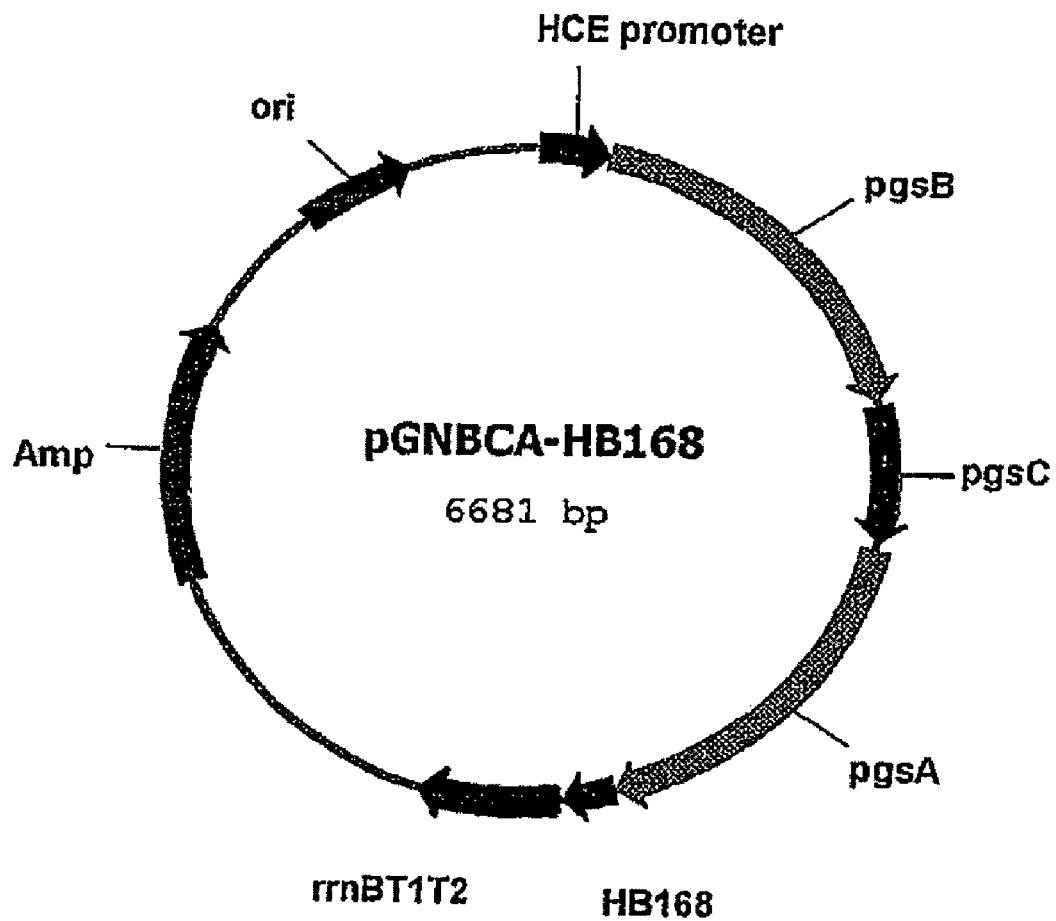
FIG. 8 depicts the genetic maps of the cloning vector pGNBCA and the recombinant vector pGNBCA-HB168 for the surface expression as described in Indirect Example of the present invention.

The primers of SEQ ID NO. 8 and SEQ ID NO. 9 described above were made to include the recognition site of restriction enzyme Bam HI and Hind III present in the surface expression vector pGNBCA. The hepatitis B virus S antigen gene amplified above was digested with the restriction enzyme Bam HI and Hind III and ligated to the C-terminus of cell outer membrane gene participating in poly-.γ-glutamate synthesis, previously prepared and adjusting the translation codon. As a result, the recombinant vector pGNBCA-HB 168 was prepared as described above (See FIG. 8)

The recombinant vector pGNBCA-HB168 for the surface expression was utilized to express the antigenic determinant forming neutralizing antibody of hepatitis B virus S antigen in *Escherichia coli* and to examine the surface expression.

The surface expression vector constructed in Example 2 was transformed to *Escherichia coli* and cultivated in 50 mL of LB medium (yeast extract 5 g/L, tryptone 10 g/L, salt 5 g/L, pH 7.0) containing 100 mg/L antibiotic (ampicillin) and then induced for the surface expression.

The antigenic determinant forming neutralizing antibody of S antigen fused with the C-terminus of poly-.γ-glutamate synthetase gene was expressed in bacteria and identified by performing SDS-polyacrylamide gel electrophoresis and western blotting with specific antibodies against S antigen. Concretely, proteins obtained in the same cell concentration were denatured to prepare a sample and analyzed by performing SDS-polyacrylamide gel electrophoresis and then, fractionated proteins were transferred to PVDF membrane. The PVDF membrane completed to transfer proteins was shaked and blocked for 1 hour by using blocking buffer (50 mM Tris HCI, 5% skin milk, pH 8.0). Afterward, the polyclonal primary antibody against S antigen derived from sheep was diluted to 1,000.times. in blocking buffer and reacted for 12 hours. The reacted membrane was washed with buffer solution and incubated for 4 hours by diluting the secondary antibody against sheep conjugated with biotin in blocking buffer to 1,000.times. The reacted membrane was washed with buffer solution and incubated with avidin-biotin reagent for 1 hour and again washed. Onto the washed membrane, H.sub.20.sub.2 and DAB solution were added as a substrate and coloring reagent and became colored so as to identify the specific binding in between specific antibody against S antigen and the above mentioned fused protein (See FIG. A). In FIG. 9, lane 1 is host cell JM109 not transformed and lane 2 is the transformant pGNBCA-HB 168/JM 109. As illustrated in Figs, approximately 48 KDa band of fused protein was verified by the plasmid pGNBCA-HB 168.

Figure 9A:
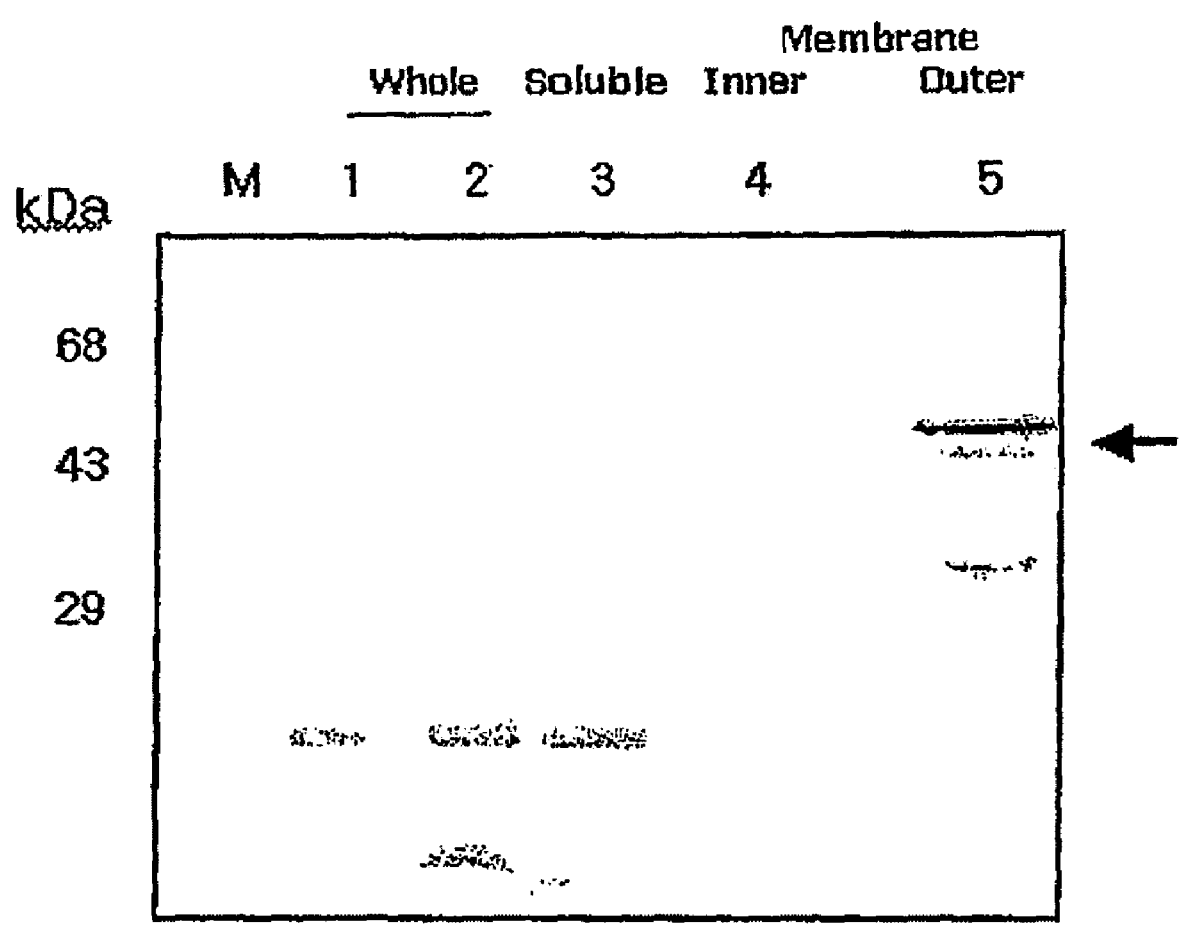
FIG. 9 depicts the surface expression of hepatitis B virus surface antigen protein from Gram negative bacterium transformed with the recombinant vector pGNBCA-HB168 by performing western blotting and fluorescent activating cell sorting flow cytometry as described in Indirect Example of the present invention.

In order to confirm the direct expression of the antigenic determinant forming neutralizing antibody of S antigen, *Escherichia coli* induced was separated respectively to soluble, inner membrane, outer membrane through the outer membrane fractionation method and then, identified by performing SDS-polyacrylamide gel electrophoresis and western blotting with antibodies against S antigen. Concretely, *Escherichia coli* transformant induced to express the fused protein onto a cell surface and *E. coli* not transformed were harvested with adjusting to the same cell concentration, washed in buffer solution (10 mM HEPES buffer, pH 7.4)

several times, suspended in buffer solution containing 10.mu.g/ml lysozyme, 1 mM PMSF and 1 mM EDTA and reacted for 4.about.10 minutes. Afterward, DNase (0.5 mg/.mu.l) and RNase (0.5 mg/ml) were added and cells were sonicated, separated to *E. coli* and cellular debris by centrifuging at 10,000.times.g for 4, 20 minutes and collected the fraction including periplasm and cytoplasm of *E. coli*. Then, the collected pellet was suspended in PBS buffer (pH 7.4) containing 1% Sarcosyl (N-lauryl sarcosinate, sodium salt), separated to inner membrane protein of *E. coli* in a supernatant and to outer membrane protein in a cell pellet by centrifuging at 15,000.times.g for 4, 2 hours and thus the fractions were obtained. Each fraction was identified by performing polyacrylamide gel electorphoresis and western blotting with antibodies against S antigen and from *E. coli* fractions the antigenic determinant forming neutralizing antibodies of S antigen was verified to exist in the outer membrane (See FIG. 9A; the result of western blot in *E. coli* membrane fraction). In FIG. 9, lane 1 is JM 109 strain not transformed; lane 2, whole cell of the transformant pGNBCA-HB168/JM 109; lane 3, soluble fraction of the transformant pGNBCA-HB168/JM109; lane 4, the outer membrane fraction of the transformant pGNBCA-HB168/JM109; and lane 5, the outer membrane fraction of the transformant pGNBCA-HB168/JM109.

It is confirmed that the antigenic determinant forming neutralizing antibody of S antigen was expressed onto *E. coli* cell surface on account of the C-terminus of poly-.γ-glutamate synthetase protein, through the fluorescence activating cell sorting (FACS) flow cytometry. For an immunofluorescence staining, *E. coli* induced was harvested to adjust the cell concentration to the same level, washed with PBS buffer (pH 7.4) several times, suspended in 1 ml buffer containing 1% bovine serum albumin, and reacted with polyclonal primary antibody against S antigen derived from sheep after diluted to 1,000.times. for 4.about.12 hours. The cells completed to react were washed several times in buffer solution, suspended in 1 ml buffer containing 1% bovine serum albumin and then reacted for 3.about.4 hours after diluting the biotin-associated secondary antibody. Again, the reacted cell was washed several times with buffer solution, suspended in 0.1 ml buffer containing 1% bovine serum albumin and then reacted with biotin-specific streptoavidin-R-phycoerythr- in, coloring reagent after diluted to 1,000-fold.

Figure 9B:
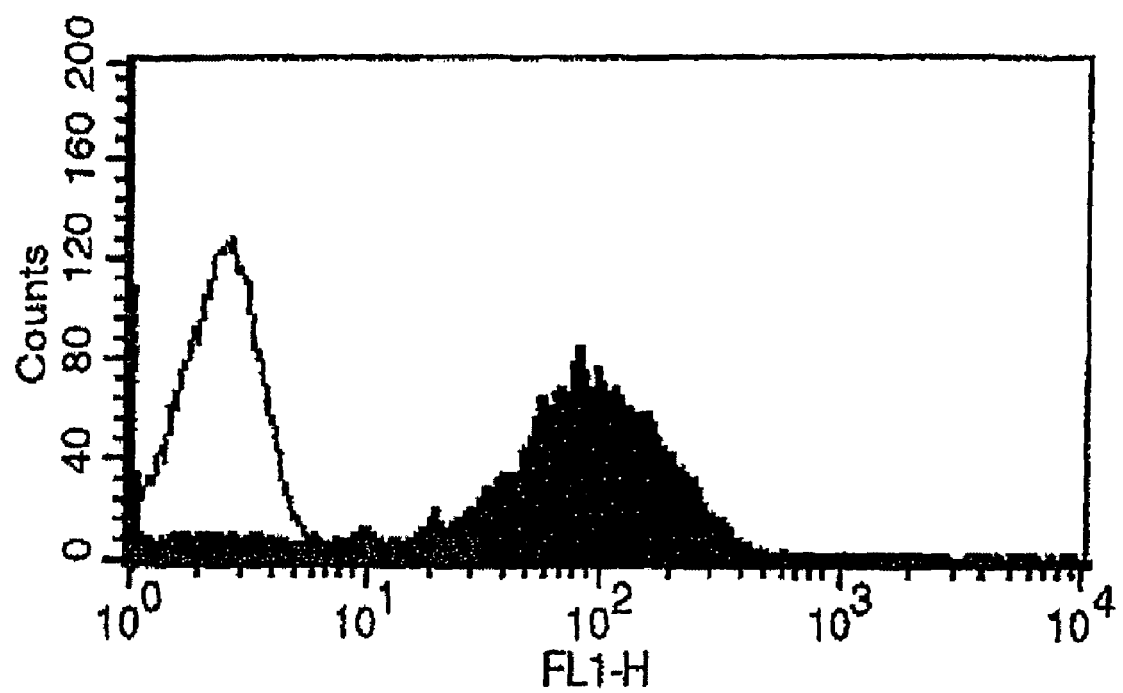

The reacted *E. coli* was washed several times and examined through the fluorescence-activating cell sorting flow cytometry. As a result, the antigenic determinant protein forming neutralizing antibody of S antigen was identified to be expressed onto a cell surface, compared with *E. coli* not transformed (See FIG. 9B). In FIG. 9B, white color is derived from JM 109 not transformed and black color, from the transformant pGNBCA-HB168/JM109. As illustrated in FIG. 9, the antigenic determinant forming neutralizing antibody of S antigen was not expressed in *E. coli* not transformed, but in *E. coli* transformant transformed with the surface expression vector, the antigenic determinant forming neutralizing antibody of S antigen was clearly verified.

Indirect Example 2

Construction of the Recombinant Vector pGNCA-HB168 and Surface Expression of the Antigenic Determinant Forming Neutralizing Antibody of Hepatitis B Virus S Antigen Cell outer membrane gene, pgs C and pgs A among pgs BCA participating in poly-.γ-glutamate synthesis derived from *Bacillus* sp. strain was utilized to construct the recombinant vector for the surface expression by using Gram negative bacterium as a host cell.

In order to obtain the gene encoding the N-termini and the C-termini of pgs C and pgs A from cell outer membrane protein participating in poly-.γ-glutamate synthetase, whole chromosome was used as a template and oligonucleotides containing the nucleotide sequences of SEQ ID NO. 10 and SEQ ID NO. 11 as a primer. Then the polymerase chain reaction was performed.

The primer corresponding to the N-terminus was made to contain the recognition site of restriction enzyme Nde I present in the expression vector pHCE 19T(II). At this moment, the amplified region has approximately 1.6 kb size from the N-terminus of pgs C to the C-terminus of pgs A which is a cell outer membrane gene participating in poly-.γ-glutamate synthesis.

The gene amplified by the polymerase chain reaction was digested with the restriction enzyme Nde I and Bam HI and inserted to the constitutively high expression vector pHCE19T(II) already digested with Nde I and Bam HI. As a result, the new vector having about 5.3 kb size was to prepared and named to pGNCA in which the cell outer membrane protein gene participating in the poly-.γ-glutamate synthesis do not have the translation termination codon and new recognition sites of restriction enzymes are added.

Figure 10:
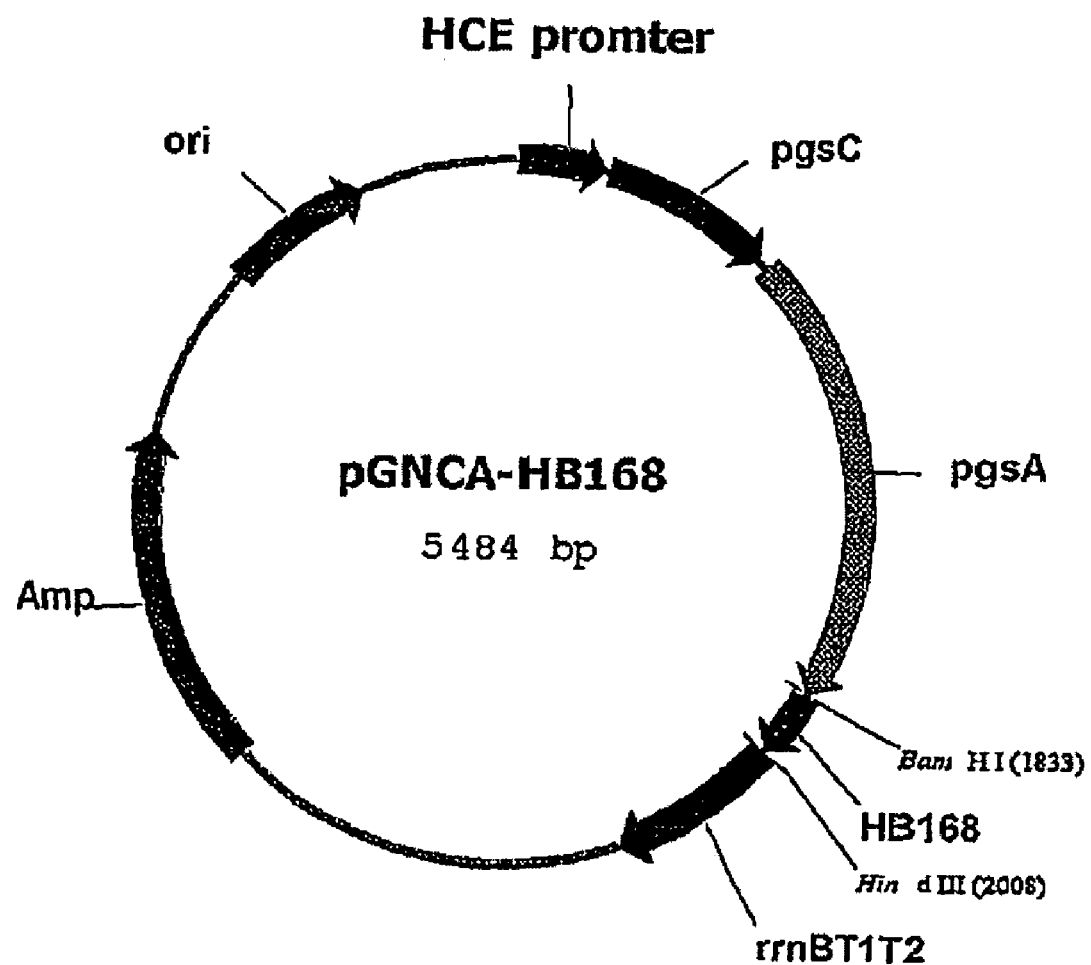
FIG. 10 depicts the genetic maps of the cloning vector pGNCA and the recombinant vector pGNCA-HB168 for the surface expression as described in Indirect Example of the present invention.

The recombinant vector pGNCA-HB168 expressing the antigenic determinant forming neutralizing antibody of hepatitis B virus S antigen onto the cell surface was constructed by using the cell outer membrane gene, pgs C and pgs A among pgs BCA participating in poly-.γ-glutamate synthesis and Gram negative bacterium as a host cell as described in Example 2. The recombinant vector pGNCA-HB 168 prepared above was illustrated in FIG. 10.

The recombinant vector pGNCA-HB168 was utilized to produce the antigenic determinant forming neutralizing antibody of hepatitis B virus S antigen in *E. coli* and examined the surface expression.

For this purpose, the recombinant vector was transformed to *E. coli* and induced to be expressed through the same process described in Example 3, and then, the antigenic determinant forming neutralizing antibody of hepatitis B virus S antigen fused with the cell outer membrane protein pgs CA was identified to be expressed by performing SDS polyacrylamide gel electrophoresis and western blotting with antibodies against S antigen.

Figure 11A:
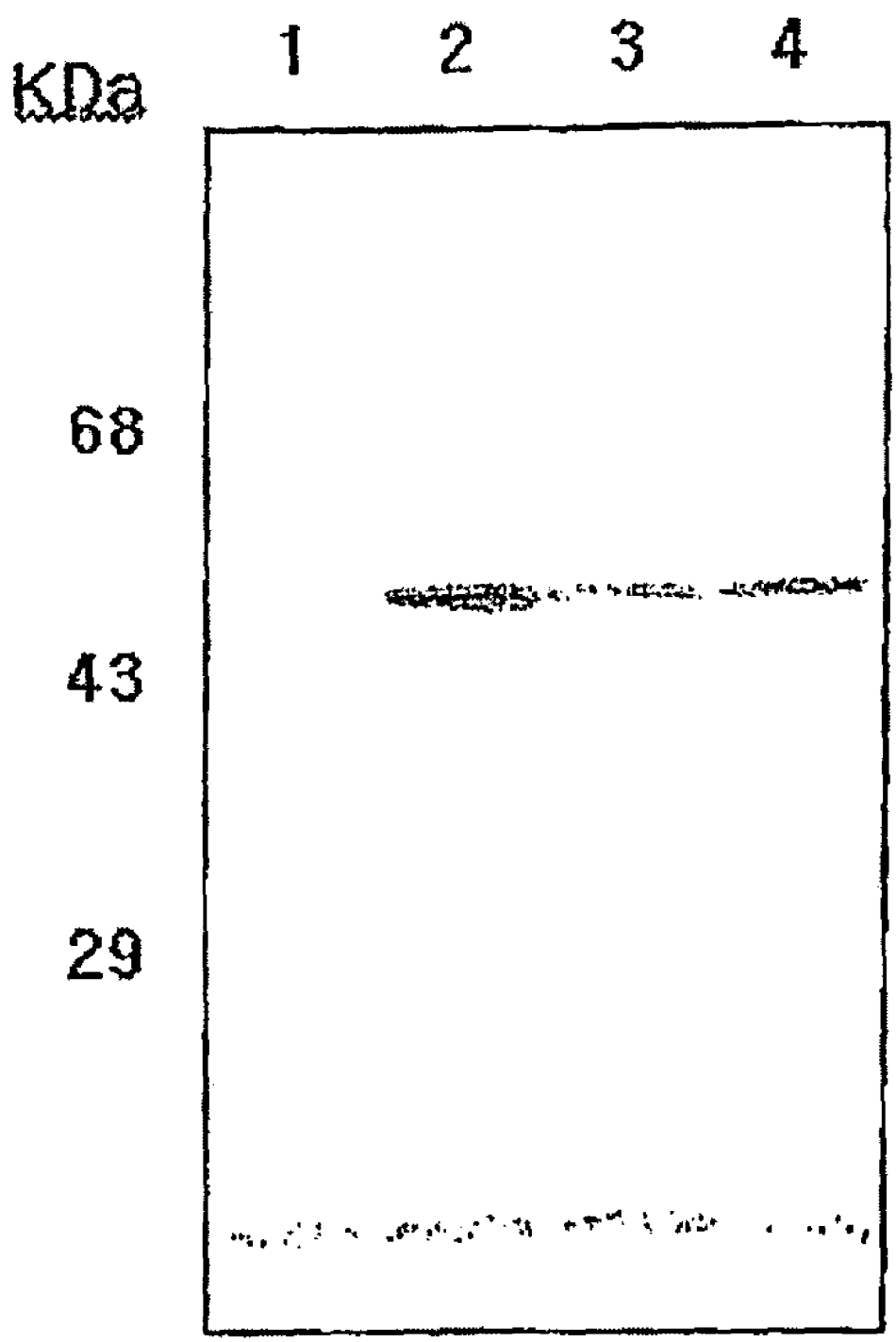
FIG. 11 depicts the surface expression of hepatitis B virus surface antigen protein from Gram negative bacterium transformed with the recombinant vectors (pGNCA-HB168:A2, pGNA-HB1 68:A3 and pGNHB-A:A4) by performing western blotting and fluorescent activating cell sorting flow cytometry as described in Indirect Example of the present invention.
Figure 11B:
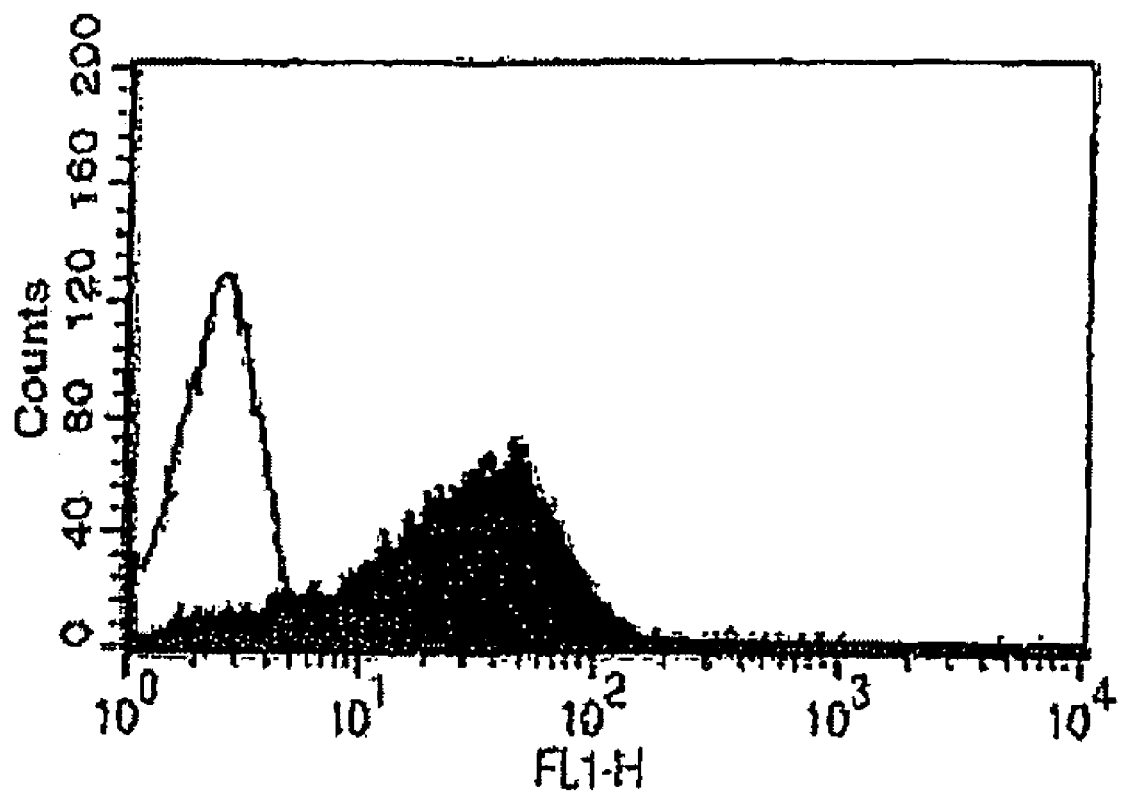

In FIG. 11, lane 1 is host cell JM 109 not transformed; lane 2 the transformed pGNCA-HB168/JM109. As illustrated in FIG. 11, approximately 48 KDa band of fused protein from the plasmid pGNCA-HB168 was verified.

INDUSTRIAL APPLICABILITY

The present inventors have developed a method for efficiently expressing capsid L1 protein of human papilloma virus onto a microbial surface by using poly-.γy-glutamate synthetase gene, pgs BCA derived from *Bacillus* sp. strain, especially onto a microbial surface of *Lactobacillus* orally administered and of Salmonella as a vaccine strain. Besides, the recombinant strain can be applied for a therapeutic and a prophylactic vaccine and the like. Since in case of HPV, the antibodies is not inductively produced in a large scale, the recombinant strain of the present invention expressing HPV antigen can be an economical vaccine such as an oral vaccine or directly applicable to vaginal legion, after proliferated in a large scale economically and chiefly.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A vector useful for preparing a vaccine, said vector including (i) one or more than two genes selected from among pgs B, pgs C and pgs A encoding poly-γ- glutamate synthetase complex and (ii) an antigen protein gene of human papilloma virus, in which said antigen protein gene is one or more than two genes selected from a group comprising capsid HPV L1 and HPV L2 of human papilloma virus.

2. The vector of claim 1, which includes a pgs A gene encoding said poly-γ-glutamate synthetase complex.

3. The vector of claim 1, which is pHCE2LB:pgsA-HPV L1.

4. A vaccine for treating or preventing mucosal tumors, comprising an active ingredient including at least one of:
   (a) a recombinant microorganism transformed with a vector including (i) one or than two genes selected from among pgs B, pgs C and pgs A encoding poly-γ-glutamate synthetase complex and (ii) an antigen protein gene of human papilloma virus, in which said antigen protein gene is one or more than two genes selected from a group comprising capsid HPV L1 and HPV L2 of human papilloma virus;
   (b) an extract from said recombinant microorganism; and
   (c) proteins purified from said recombinant microorganism.

5. The vaccine of claim 4, which is adapted to be administered orally or be edible.

6. The vaccine of claim 4, which is adapted to be injected subcutaneously or peritoneally.

7. The vaccine of claim 4, which is adapted to be sprayed to the nasal cavity.

8. A vaccine of claim 5, which comprises a recombinant microorganism transformed with the vector pHCE2LB: pgsA-HPV L1.

9. The vaccine of claim 8, which is adapted to be administered orally or be edible.

10. The vaccine of claim 8, which is adapted to be injected subcutaneously or peritoneally.

11. The vaccine of claim 8, which is adapted to be sprayed to the nasal cavity.

12. A washing solution for a genital organ, which includes as an effective component, a recombinant microorganism transformed with the vector pHCE2LB: pgsA-HPV L1.

13. A recombinant bacterium, which is selected from the group consisting of:
   (a) a recombinant Gram negative bacterium transformed with a vector including (i) one or more than two gene selected from among pgs B, pgs C and pgs A encoding poly-γ-glutamate synthetase complex and (ii) an antigen protein gene of human papilloma virus, in which said antigen protein gene is one or more than two genes selected from a group comprising capsid HPVL1 and HPVL2 of human papilloma virus;
   (b) a recombinant bacterium transformed with the vector pHCE2LB: pgsA-HPV L1; and
   (c) an a recombinant *Escherichia coli* transformed with the vector KCTC 10349 BP.

14. The recombinant bacterium of claim 13, wherein said bacterium is a Gram negative bacterium selected from among *Escherichia coli, Salmonella typhi, Salmonella typimurium, Mycobacterium bovis*, and *Shigella*.

15. The recombinant bacterium of claim 13, which is transformed with the vector pHCE2LB: pgsA-HPV L1.

16. The recombinant bacterium of claim 13, wherein said bacterium is *Salmonella*.

17. The recombinant bacterium of claim 13, which is a recombinant *Escherichia coli* transformed with the vector KCTC 10349 BP.

* * * * *